United States Patent
Wu et al.

(10) Patent No.: US 8,709,806 B2
(45) Date of Patent: Apr. 29, 2014

(54) EPCAM AS A REPROGRAMMING FACTOR FOR NON-PLURIPOTENT CELLS

(75) Inventors: Han-Chung Wu, Taipei (TW); Tung-Ying Lu, Kaohsiung (TW); Cheng-Fu Kao, Taipei (TW); John Yu, Taipei (TW); Ruei-Min Lu, Sanchong (TW); Mei-Ying Liao, Wufeng Township (TW); Hung-Chih Kuo, Matou (TW)

(73) Assignee: Academia Sinica, Taipei (TW)

( * ) Notice: Subject to any disclaimer, the term of this patent is extended or adjusted under 35 U.S.C. 154(b) by 430 days.

(21) Appl. No.: 12/930,154

(22) Filed: Dec. 28, 2010

(65) Prior Publication Data

US 2011/0275105 A1    Nov. 10, 2011

Related U.S. Application Data

(60) Provisional application No. 61/335,118, filed on Dec. 30, 2009.

(51) Int. Cl.
  *C12N 15/00* (2006.01)
  *C12N 15/02* (2006.01)
(52) U.S. Cl.
  USPC ............ 435/377; 435/373; 435/383; 435/455
(58) Field of Classification Search
  None
  See application file for complete search history.

(56) References Cited

PUBLICATIONS

Stadtfeld et al. Induced Pluripotent Stem Cells Generated Without Viral Integration. Science, 2008, vol. 322, pp. 945-949.*
Okita et al. Generation of Mouse Induced Pluripotent Stem Cells Without Viral Vectors. Science, vol. 322, pp. 949-955.*
Gonzales et al. Generation of mouse-induced pluripotent stem cells by transient expression of a single nonviral polycistronic vector. PNAS, 2009, vol. 106, pp. 8918-8922.*
Miyamoto et al. Reprogramming Events of Mammalian Somatic Cells Induced by Xenopus laevis Egg Extracts. Molec. Reprod. Devel., 2007, vol. 74, pp. 1268-1277.*
Stojovic et al. Derivation, growth and applications of human embryonic stem cells. Reproduction, 2004, vol. 128, pp. 259-267.*
Strelchenko et al. Embryonic Stem Cells From Morula. Methods in Enzym., 2006, vol. 418, pp. 93-108.*
Xu et al. Feeder-free growth of undifferentiated human embryonic stem cells. Nature Biotech., 2001, vol. 19, pp. 971-974.*
Ng; et al., "Characterization of Epithelial Cell Adhesion Molecule as a Surface Marker on Undifferentiated Human Embryonic Stem Cells", Stem Cells (2010), 28(1)29-35.

* cited by examiner

*Primary Examiner* — Deborah Crouch
(74) *Attorney, Agent, or Firm* — Bozicevic, Field & Francis; Pamela J. Sherwood

(57) ABSTRACT

Methods are provided for inducing non-pluripotent cells to become pluripotent. Methods also include identifying and isolating induced pluripotent (iPS) cells and uses thereof. Compositions and kits for carrying out the subject methods are also provided.

5 Claims, 10 Drawing Sheets
(2 of 10 Drawing Sheet(s) Filed in Color)

A

B

C

EPCAM AS A REPROGRAMMING FACTOR FOR NON-PLURIPOTENT CELLS

INTRODUCTION

Stem cells are defined as cells that, at the single cell level, are capable of both self-renewal and differentiation to specialized cell types. Human embryonic stem cells (hESCs) retain the unlimited proliferation and developmental pluripotency from their progenitors and are able to self-renew and give rise to differentiated progeny of all three germ layers. The ability of pluripotent cells to grow specialized cells and tissues could provide an unprecedented tool in the clinic, by providing a means for transplantation and repair of damaged muscles, nerves, organs, bones and other tissues. Therefore, pluripotent cells have potential clinical applications and can be used to explore our knowledge of basic developmental biology and there remains a need for a method to induce cells to become induced pluripotent stem (iPS) cells.

SUMMARY OF THE INVENTION

Methods are provided for inducing a non-pluripotent cell (e.g. somatic cell) to become a pluripotent stem cell. The methods involve introducing epithelial cell adhesion (Ep-CAM) activity to a non-pluripotent cell, e.g. by introducing into the non-pluripotent cell a vector encoding EpCAM operably linked to a promoter active in the cell, etc. Optionally one or more additional reprogramming factors are introduced in combination with EpCAM. The methods may further involve screening for the presence of cells having stem cell potential (e.g. using an antibody specific for pluripotent cells), including cells expressing EpCAM. The methods may also involve isolating stem cells.

Kits are also provided in the present disclosure. The kits contain compositions for inducing non-pluripotent cell into induced pluripotent cells (iPS) and reagents needed for carrying out the subject methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 7:
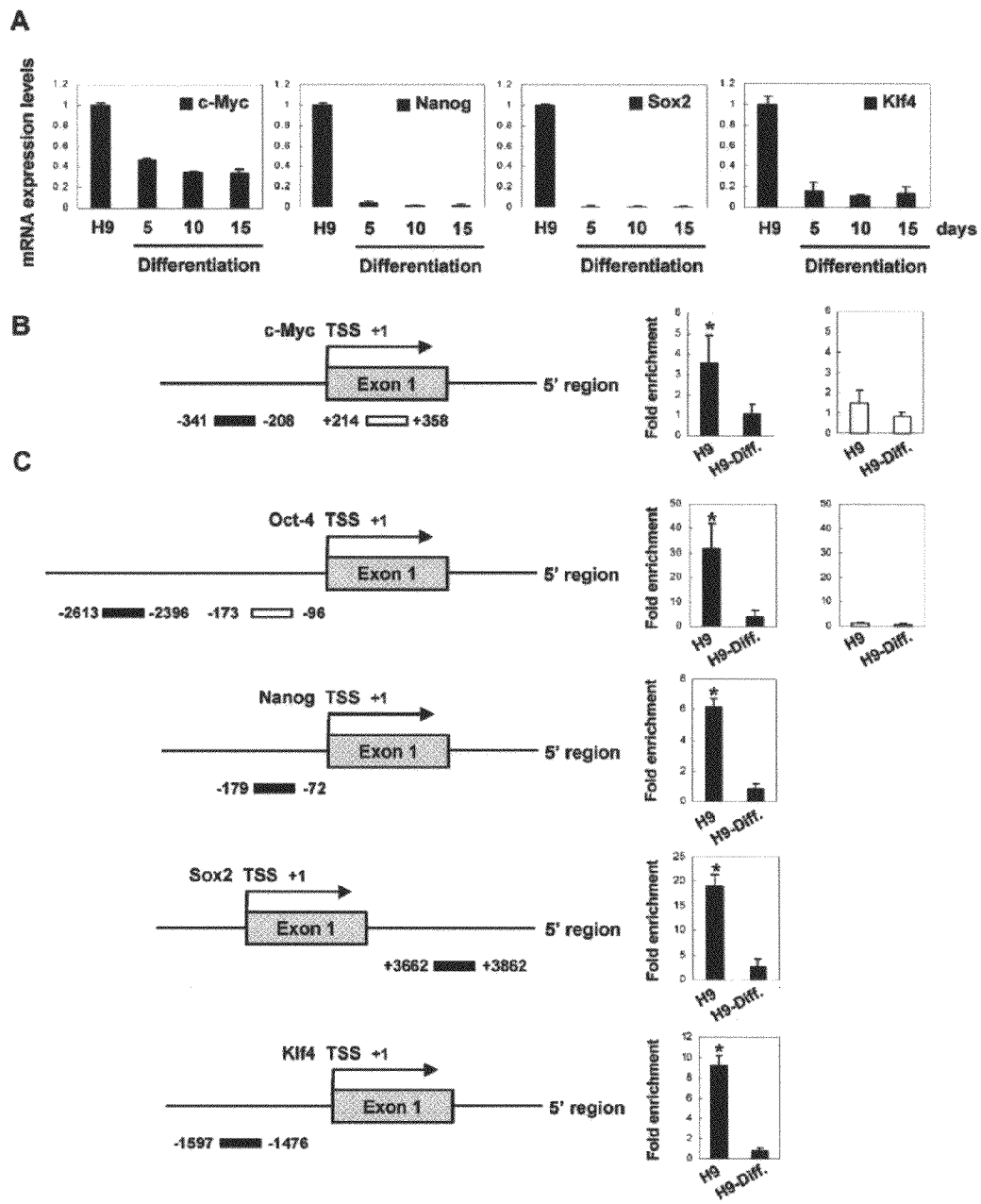
Figure 7:
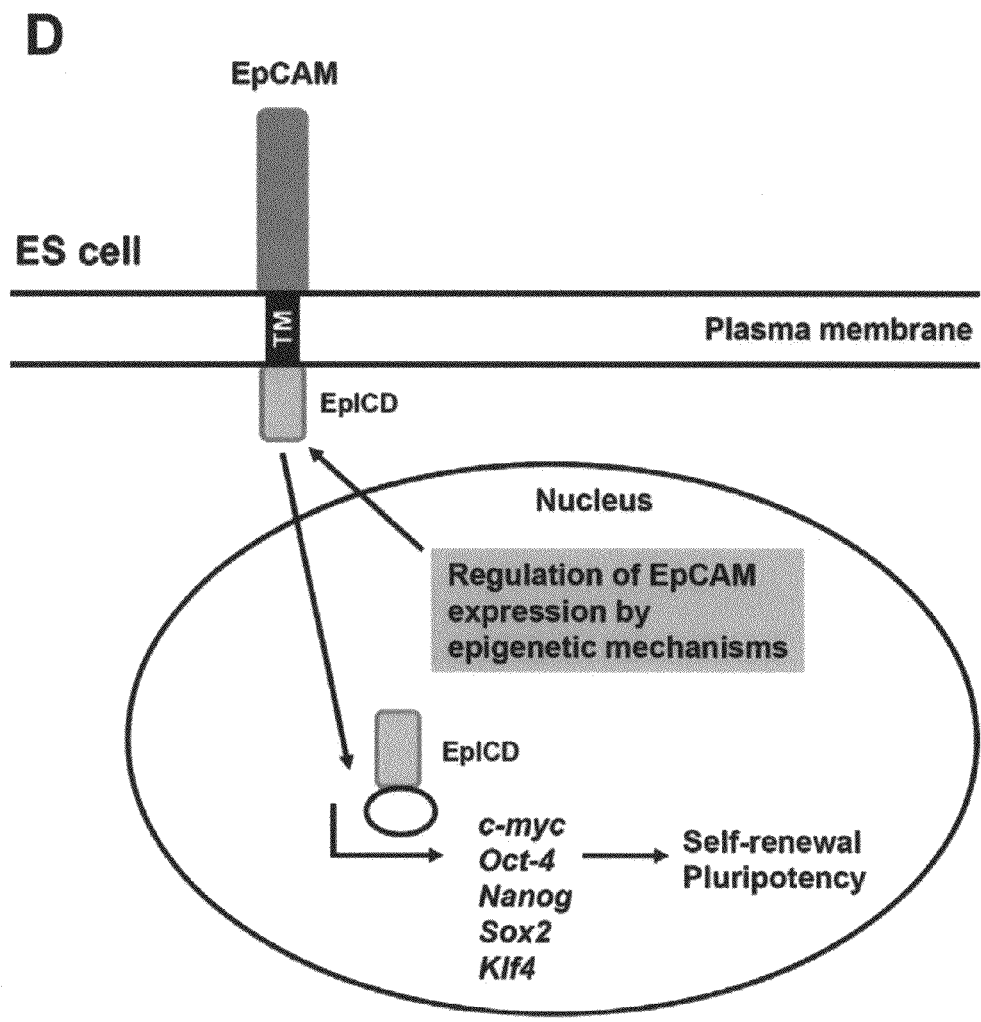

FIG. 7. EpCAM regulates c-Myc, Oct-4, Nanog, Sox2 and Klf4 to help maintain sternness in hESCs. A: Q-RT-PCR analysis of c-Myc, Nanog, Sox2 and Klf4 mRNA expression in undifferentiated H9 cells and in H9 cells differentiated for 5, 10, and 15 days, the expression level was normalized to internal control GAPDH. B: Quantitative ChIP analysis of EpCAM binding to c-Myc promoter (*, P<0.05). C: Quantitative ChIP analysis of EpCAM binding to Oct-4, Nanog, Sox2 and Klf4 promoters (*, P<0.05). D: Schematic illustration of signaling pathways of EpCAM. EpCAM expression in hESCs is controlled by epigenetic regulation. The signaling of EpCAM was achieved by EpICD translocation into the nucleus, which contacted promoters of c-Myc, Oct-4, Nanog, Sox2 and Klf4 to exert its impact on maintaining ES cell sternness condition.

Figure 8:
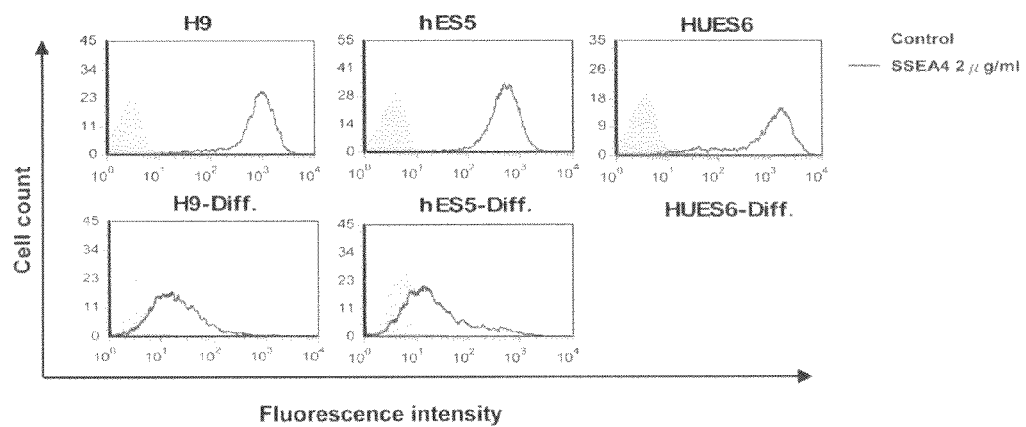

FIG. 8. Confirmation of undifferentiated and differentiated hESCs by measuring cell surface SSEA4 expression. Cell surface SSEA4 protein expression by undifferentiated (H9, hES5 and HUES6) and differentiated (H9-Diff., hES5-Diff. and HUES6-Diff.) hESCs were investigated by flow cytometric analysis using an anti-SSEA4 MAb. Fluorescence minus control without addition of the anti-SSEA4 antibody was used as a negative control (grey histogram).

Figure 9:
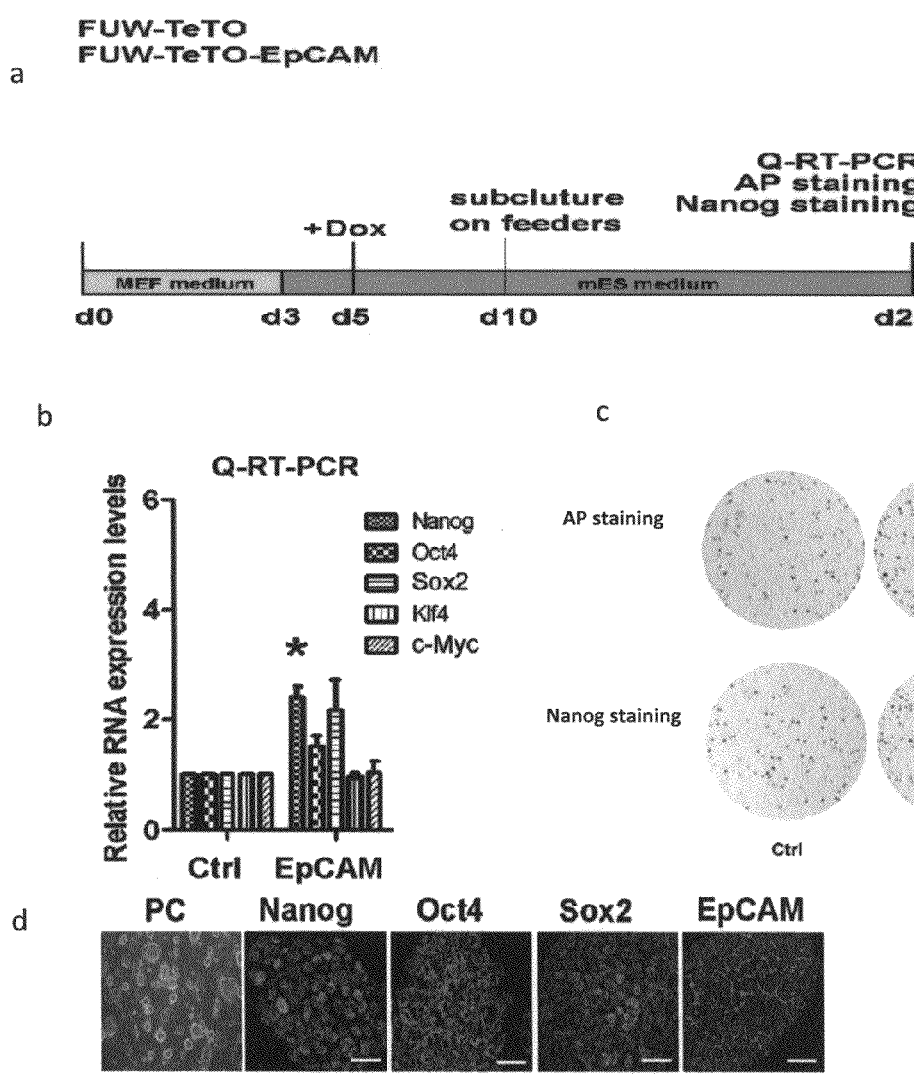

FIG. 9. Overexpression of EpCAM, enhanced OSKM-mediated reprogramming. (a) Schematic representation of the OSKM-mediated reprogramming process with overexpression of EpCAM. Dox, doxycycline (b) Q-RT-PCR analysis for indicated pluripotency-related genes at day 25 after transducing MEFs with lentiviruses containing OSKM and EpCAM. The RNA level of each gene was normalized to its counterpart in the control group. Data are presented as mean±S.E.M., n=4; *P<0.05. (c) AP staining and Nanog immunostaining by DABconducted on MEFs at day 25 of reprogramming with or without overexpression of EpCAM protein encoding genes. (d) EpCAM and OSKM derived iPSC expressed pluripotent-related markers as indicated.

DEFINITIONS

In the description that follows, a number of terms conventionally used in the field of cell culture are utilized extensively. In order to provide a clear and consistent understanding of the specification and claims, and the scope to be given to such terms, the following definitions are provided.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

Stem cell: The term stem cell is used herein to refer to a mammalian cell that has the ability both to self-renew, and to generate differentiated progeny. The ability of generate differentiated progeny may be described as pluripotent (see Morrison et al. (1997) Cell 88:287-298). As such, stem cells and pluripotent cells may be used interchangeably in the present disclosure. Generally, stem cells also have one or more of the following properties: an ability to undergo asynchronous, or asymmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages.

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPS cells" it is meant that the differentiated somatic cells can be induced to become, i.e. can be reprogrammed to become, iPS cells. In other words, the somatic cell can be induced to redifferentiate so as to establish cells having the morphological characteristics, growth ability and pluripotency of pluripotent cells. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

The terms "primary cells", "primary cell lines", and "primary cultures" are used interchangeably herein to refer to cells and cells cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

The term "efficiency of reprogramming" is used to refer to the ability of a primary cell culture to give rise to iPS cell colonies when contacted with reprogramming factors. Primary cell cultures which demonstrate an enhanced efficiency of reprogramming will demonstrated an enhanced ability to give rise to iPS cells when contacted with reprogramming factors relative to a control. For example, primary cell cultures of the present invention that demonstrate an enhanced efficiency of reprogramming will demonstrated an enhanced ability to give rise to iPS cells when contacted with reprogramming factors relative to an unselected population. By enhanced, it is meant that the primary cells or primary cell cultures have the ability to give rise to iPS cells that is about 150% of the ability of the unselected population, about 200%, about 300%, about 400%, about 600%, or about 800% of the ability of the unselected population. In other words, the primary cells or primary cell cultures produce about 1.5-fold, about 2-fold, about 3-fold, about 4-fold, about 6-fold or about 8-fold the number of iPS colonies as the unselected population, or more. Typically, the methods of the invention provide for an increased efficiency of reprogramming that is at least about two-fold or higher.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells of the subject invention individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc. In addition, stem cells encompass those that may be derived from a natural source or artificially derived in a laboratory environment.

As used herein, "induced pluripotent stem cells", abbreviated as iPS cells, are a type of pluripotent stem cell artificially derived from a non-pluripotent cell, typically an adult somatic cell, by inducing expression of certain genes (e.g. injection of an expression construct). Induced pluripotent stem cells are identical in many respects to natural pluripotent stem cells, such as embryonic stem (ES) cells (e.g. in their physical properties). They may be the same in their expressions of certain stem cell genes and proteins, chromatin methylation patterns, doubling time, embryoid body formation, teratoma formation, viable chimera formation, and potency and differentiability. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of the present methods could not give rise to all types of cells in the organism.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. Human ES cell lines express cell surface markers that characterize undifferentiated nonhuman primate ES and human EC cells, including stage-specific embryonic antigen SSEA-3, SSEA-4, TRA-I-60, TRA-1-81, Sox2, and Oct-4.

An "antibody" is a molecule that recognizes and specifically binds to a target, such as a protein, polypeptide, peptide, carbohydrate, polynucleotide, lipid, etc. An antibody may bind to its target through an antigen recognition site within the variable region of the immunoglobulin molecule (e.g. heavy chain hypervariable region $V_H$ and/or light chain hypervariable region $V_L$). As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, dibodies, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

The term "cell surface antigen" (or "cell surface epitope") refers to an antigen (or epitope) on surface of a cell that is extracellularly accessible on the cell. "Extracellularly accessible" in this context refers to an antigen that can be bound by an antibody provided outside the cell without need for permeabilization of the cell membrane.

That an antibody "specifically binds" to or shows "specific binding" towards an epitope means that the antibody reacts or associates more frequently, more rapidly, with greater duration, and/or with greater affinity with the epitope than with alternative substances. As used herein, "specifically binds" means that an antibody binds to a protein with a $K_D$ of at least about 0.1 mM, at least about 1 µM, at least about 0.1 µM or better, or 0.01 µM or better.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

"Isolated" in regard to cells, refers to a cell that is removed from its natural environment (such as in a heterogeneous population) and that is isolated or separated, and is at least about 30%, 50%, 75% free, or about 90% free, from other cells with which it is naturally present, but which lack the marker based on which the cells were isolated. An antibody against a specific stem cell marker can be used to generate isolated populations of stem cells.

"Amino acid sequence" and terms such as "polypeptide", "protein", or "peptide" are not meant to limit the amino acid sequence to the complete, native amino acid sequence associated with the recited protein molecule.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Conservative amino acid substitutions in the context of an antibody disclosed herein are selected so as to preserve the interaction between the antibody and the stem cell marker of interest.

The term "native protein" as used herein to indicate that a protein does not contain amino acid residues encoded by vector sequences; that is, the native protein contains only those amino acids found in the protein as it occurs in nature. A native protein can be produced by recombinantly or can be isolated from a naturally occurring source.

As used herein, the term "stem cell marker(s)", refers to an agent (e.g. antibody) whose binding or a protein, polypeptide, or peptide expressed by the gene or genes whose expression level, alone or in combination with other genes, is correlated with the presence of stem cells compared to differentiated cells. The correlation can relate to either an increased or decreased expression of the gene (e.g. increased or decreased levels of mRNA or the peptide encoded by the gene).

DESCRIPTION OF EMBODIMENTS

Methods of Inducing Pluripotency

Methods are provided to produce pluripotent cells. Non-pluripotent cells are reprogrammed so as to establish cells having the morphological characteristics, growth ability, and pluripotency of pluripotent cells. Cells that can be induced to be pluripotent using the subject methods include somatic cells (e.g. human differentiated cells). Also provided are methods for isolating and screening pluripotent cells. The induced pluripotent stem (iPS) cells that are made by the subject methods are useful in transplantation; for drug screening; experimental models of cellular differentiation and interaction; screening in vitro assays to define growth and differentiation factors, and to characterize genes involved in cell development and regulation; and the like. These iPS cells may be used directly for these purposes, or they may be genetically modified to provide altered capabilities.

To induce pluripotency in non-pluripotent cells, the method involves introducing epithelial cell adhesion molecule (EpCAM) activity to non-pluripotent (e.g. differentiated somatic) cells. EpCAM is a type I transmembrane glycoprotein that can reprogram cell to multipotency or to pluripotency. An EpCAM polypeptide is a polypeptide comprising an amino acid sequence that is at least 70%, at least 75%, at least 80%, at least 85%, at least 97%, at least 98%, at least 99%, or 100% identical to the amino acid sequence of human EpCAM, also known as EPCAM_HUMAN (Accession No. P16422). The amino acid sequences and encoding nucleic acid sequences of human EpCAM may be found at GenBank as Accession Nos. NP_002345 and NM_002354, respectively. EpCAM used in the present methods encompass human EpCAM, naturally occurring variants and isoforms, EpCAM homologs of non-human species, fragments thereof, and the nucleic acids that encode them. Nucleic acids encoding EpCAM encompass those that encode fragments, full-lengths, variants, isoforms, conjugates and/or fusion protein of EpCAM.

Introducing EpCAM into nonpluripotent (e.g. somatic) cells may involve administering EpCAM polypeptide directly to the cells or introducing nucleic acids encoding EpCAM to the cells.

Where the EpCAM is introduced as an encoding nucleic acid, there are many methods known in the art to carry out such introduction. Methods for introducing genetic material into cells include, for example, transformation, electroporation, conjugation, calcium phosphate, lipofection methods and the like. The method for transfer can be selected so as to provide for stable expression of the introduced EpCAM-encoding nucleic acid. When EpCAM gene synthesis is induced in the transfected cell, the produced EpCAM may be detected by assaying binding of an antibody specific for cells. Antibodies specific for EpCAM can be used to identify cells that express EpCAM detectable on the cellular surface. Cells expressing EpCAM can be isolated using techniques known in the art.

Nucleic acids encoding EpCAM may be provided directly to the cells. Vectors useful for transferring exogenous genes into target mammalian cells can be used in the subject methods to introduce EpCAM. The EpCAM-encoding vector can be provided as an inheritable episomal element (e.g., plasmid) or can be genomically integrated. A variety of appropriate vectors for use in production of EpCAM are available commercially. The vectors may be maintained episomally, e.g. as plasmids, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Vectors used for providing EpCAM to the subject cells as nucleic acids will contain suitable promoters for driving the expression, that is, transcriptional activation, of the EpCAM-encoding nucleic acids. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing EpCAM to the cells may include genes that can later be removed, e.g. using a recombinase system such as Cre/Lox, or the cells that express them destroyed, e.g. by including genes that allow selective toxicity such as herpesvirus TK, bcl-xs, etc. For example, EpCAM expression may be turned off to induce differentiation of an iPS cell.

Where nucleic acids encoding EpCAM are provided to the cells via a virus, the differentiated somatic cells are contacted with viral particles comprising nucleic acids encoding EpCAM. Retroviruses, for example, lentiviruses, are suitable to the method of the invention, as they can be used to transfect non-dividing cells. Commonly used retroviral vectors are "defective", i.e. unable to produce viral proteins required for productive infection. Rather, replication of the vector requires growth in a packaging cell line.

To generate viral particles comprising nucleic acids encoding EpCAM, the retroviral nucleic acids comprising the nucleic acid encoding EpCAM are packaged into viral capsids by a packaging cell line. Different packaging cell lines provide a different envelope protein to be incorporated into the capsid, this envelope protein determining the specificity of the viral particle for the cells. Methods of introducing the retroviral vectors comprising the nucleic acid encoding EpCAM into packaging cell lines and of collecting the viral particles that are generated by the packaging lines are well known in the art.

Where EpCAM are introduced directly as a polypeptide to nonpluripotent cells, the EpCAM may be introduced by various protein transduction methods known in the art. In some cases, the protein transduction method includes contacting cells with a composition containing a carrier agent known in the art and the EpCAM polypeptide.

The EpCAM polypeptide may also be presented to the cell with or without conjugation. The EpCAM may be fused to a polypeptide permeant domain. A number of permeant domains are known in the art and may be used in the nuclear acting, non-integrating polypeptides of the present invention, including peptides, peptidomimetics, and non-peptide carriers. Other peptide or non-peptide conjugate that enhance the delivery of polypeptides known in the art may be used in the subject methods.

Other conjugates may be fused to EpCAM include those that increase solubility or half-life of EpCAM. EpCAM may also be conjugated to a detectable label. Linkers may optionally be used in making fusion EpCAM and/or EpCAM conjugates may include one or more flexible sequences, e.g. from 1 to 10 glycine residues. Methods of making EpCAM polypeptides are discussed later below.

EpCAM can be provided to the cells once (via the nucleic acid encoding EpCAM or EpCAM directly), and the cells are allowed to incubate with EpCAM for several number of hours, after which time the media is replaced with fresh media and the cells are cultured further. EpCAM may also be provided to the cells twice, or more times. In contacting cells with EpCAM, the cells may be incubated with EpCAM for various lengths of times. for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours. The contacting may also be repeated with a frequency of about every day to about every 4 days, e.g., every 1.5 days, every 2 days, every 3 days, or any other frequency from about every day to about every four days. Such parameters are provided as examples and may be determined through routine trials.

After contacting the cells with EpCAM, the contacted cells are cultured so as to promote the outgrowth of iPS cells. Methods for culturing cells to promote the growth of pluripotent cells, isolating pluripotent cell clones and culturing cells of those pluripotent cell clones so as to promote the outgrowth of pluripotent cells are well known in the art, any of which may be used in the present methods to grow, isolate and reculture the iPS cells from the reprogrammed differentiated somatic cells.

Characterization and Isolation of Pluripotent Cells

In order to verify that a differentiated somatic cell has been genetically modified to be an iPS cell, various techniques may be employed. Methods described herein for verifying pluripotency can also be used to monitor response to therapy and to aid in prognosis.

One way to verify pluripotency is to carry out gene expression analysis to see if the expression profile corresponds to those of a pluripotent cell. Assays include but not limited to polymerase chain reaction; gel electrophoresis; restriction analysis; Southern, Northern, and Western blots; sequencing; or the like. The cells may be grown under various conditions to ensure that the cells are capable of maturation to all of the myeloid lineages while maintaining the ability to express the introduced DNA. Various tests in vitro and in vivo may be employed to ensure that the pluripotent capability of the cells has been maintained. The desired cells can be identified by their surface phenotype, by the ability to self-renew, ability to form differentiated cells, etc. The cells to be analyzed may be viable cells, or may be fixed or embedded cells (e.g. from clinical samples from a recipient of iPS).

Pluripotent stem cells are identified by their phenotype with respect to particular markers, and/or by their functional phenotype. The iPS cells can be identified and/or isolated by binding to the cell with reagents specific for the markers of pluripotency. iPS cells derived from the differentiated somatic cell population have an hESC-like morphology, growing as flat colonies with large nucleo-cytoplasmic ratios, defined borders and prominent nuclei. In addition, the iPS cells express one or more key pluripotency markers known by one of ordinary skill in the art, including but not limited to Klf4, SSEA3, SSEA4, Sox2, Oct3/4, and/or Nanog. They are capable of forming or contributing to ectoderm, mesoderm, or endoderm tissues in a living organism. In addition, the iPS cells are capable of forming teratomas.

In isolating and maintaining iPS cells, other genes may be introduced for a variety of purposes, e.g. to replace genes having a loss of function mutation, provide marker genes, etc. Alternatively, vectors can be introduced that express antisense mRNA or ribozymes, thereby blocking expression of an undesired gene to maintain sternness, for example. Other methods of gene therapy include the introduction of drug resistance genes to enable selection and further purification. For example, multiple drug resistance gene (MDR) or anti-apoptosis genes (e.g. bcl-2) can be introduced to the pluripotent cells to have an advantage when subjected to selective pressure.

The reagents specific for iPS that may be used in characterization and isolating include antibodies, which may be directly or indirectly labeled. A reporter, e.g. LacZ, can also be operably connected to an endogenous promoter that is known to be activated in a pluripotent cell, thereby providing a marker.

Use of Antibody Specific for EpCAM

Techniques used to verify and isolate a pluripotent cell transformed using the subject methods may involve using an antibody specific to EpCAM (e.g. an epitope in the extracellular domain of EpCAM). The antibodies (e.g. OC98-1 used in the Examples below) may be used to precipitate or bind to the corresponding native EpCAM (or exogenous EpCAM) in a pluripotent cell to facilitate isolation. When transplanted in an organism for example, the iPS can also be identified using antibodies specific for EpCAM. The antibody can be used to identify EpCAM-expressing cells in a tissue sample or for in vivo imaging, etc. The tissue sample under examination using the antibodies may also be fixed (e.g., by formalin treatment) and may be provided embedded in a support (e.g., in paraffin) or frozen unfixed tissue.

Antibodies used herein may be conjugated to a label. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red. Where more than one antibody is used, each antibody may be distinguishably labeled, such as with a different fluorochrome, to permit independent sorting for each marker.

Assays involving the use of an antibody specific for pluripotent cells (e.g. antibody against EpCAM) can take a variety of forms, such as competition, direct reaction, sandwich type assays, or fluorescence activated cell sorters. Examples of assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between EpCAM in the sample and the antibody or antibodies reacted therewith.

The assays can involve separation of unbound antibody in a liquid phase from a solid phase support to which antigen-antibody complexes are bound. Solid supports which can be used include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Pluripotent Cells and Compositions Thereof

Pluripotent cells may be separated from a population of cells with heterogeneous pluripotency by techniques that enrich for cells that differentially express EpCAM using methods described above.

Compositions highly enriched for iPS cells generated by the present methods may be at or about 50% or more of the cell composition, and preferably be at or about 75% or more of the cell composition, and may be 90% or more. The enriched cell population may be used immediately, or may be frozen at liquid nitrogen temperatures and stored for long periods of time, being thawed and capable of being reused. The cells may be stored in 10% DMSO, 90% FCS medium. The population of cells enriched for stem cells may be used in a variety of screening assays and cultures, as described later below.

The enriched pluripotent cell population may be maintained in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI 1640, optionally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non polypeptide factors. A wide variety of growth factors may be used in culturing the cells, e.g. LIF, NGF, steel factor (c-kit ligand), EGF, insulin, IGF, Flk-2 ligand, IL-11, IL-3, GM-CSF, erythropoietin, thrombopoietin, etc.

In addition to, or instead of growth factors, the subject cells may be grown in a co-culture with fibroblasts, stromal or other feeder layer cells. Stromal cells suitable for use in the growth of stem cells are known in the art.

Screening Assays Using iPS Cells

The pluripotent cells isolated by the methods of the present disclosure find use in compound screening, screening to identify genes expressed in pluripotent cells, screening for therapies utilizing stem cells, and the like.

Screening may be performed using an in vitro model, a cell manipulated in accordance with the subject methods, animal containing thereof, or purified stem cells. Transgenic animals or cells derived therefrom can also used in compound screening.

Screening identifies compounds or genes that modulate function of the pluripotent cells, e.g. to maintain pluripotency or to induce differentiation into specific cell type. Of particular interest are screening assays for compounds that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, e.g. protein or pharmaceutical, with the capability of altering or mimicking the physiological function of EpCAM, or the maintenance of sternness. Generally a plurality of assay mixtures are run in parallel with different agent concentrations to obtain a differential response to the various concentrations.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries are known in the art.

Compounds that are initially identified by any of the foregoing screening methods can be further tested to validate the apparent activity. The basic format of such methods involves administering a lead compound identified during an initial screen to an animal that serves as a model for humans and then determining activity. The animal models utilized in validation studies generally are mammals. Specific examples of suitable animals include, but are not limited to, primates, mice, and rats.

Differentiating iPS Cell

The iPS cells produced by the above methods may be used for reconstituting or supplementing differentiating or differentiated cells in a recipient. The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more of the following: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the induced cells may be terminally differentiated cells, or they may be capable of giving rise to cells of a specific lineage. For example, induced cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo. Differentiation may involve silencing the expression of endogenous and/or exogenous EpCAM. Methods known in the art involve either culturing iPS with one or more factors or inhibiting the activity or expression of one or more proteins.

For iPS cells that have undergone differentiation, subpopulations of differentiated cells may need be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter.

Methods of Treatment

The iPS cells, or cells differentiated from the induced cells, may be used as a therapy to treat disease (e.g., a genetic defect). The method involves administering iPS cells generated by the present method or cell differentiated from such iPS cells to a patient (e.g. human patient). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid. The iPS cells may be administered in any physiologically acceptable medium. They may be provided alone or with a suitable substrate or matrix, e.g. to support their growth and/or organization in the tissue to which they are being transplanted.

The induced cells may be differentiated into cells and then transferred to subjects suffering from a wide range of diseases or disorders. Subjects suffering from neurological diseases or disorders could especially benefit from stem cell therapies. In some approaches, the induced cells may be differentiated into neural stem cells or neural cells and then transplanted to an injured site to treat a neurological condition, e.g., Alzheimer's disease, Parkinson's disease, multiple sclerosis, cerebral infarction, spinal cord injury, or other central nervous system disorder.

Diseases other then neurological disorders may also be treated by a stem cell therapy that uses cells differentiated from induced cells, e.g., induced multipotent or pluripotent stem cells. Degenerative heart diseases such as ischemic cardiomyopathy, conduction disease, and congenital defects could benefit from stem cell therapies.

Pancreatic islet cells (or primary cells of the islets of Langerhans) may be transplanted into a subject suffering from diabetes (e.g., diabetes mellitus, type 1), see e.g., Burns et al., (2006) Curr. Stem Cell Res. Ther., 2:255-266.

In other examples, hepatic cells or hepatic stem cells derived from induced cells are transplanted into a subject suffering from a liver disease, e.g., hepatitis, cirrhosis, or liver failure.

Hematopoietic cells or hematopoietic stem cells (HSCs) derived from induced cells may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma.

In some cases, the induced cells are transferred into an immunocompromised animal, e.g., SCID mouse, and allowed to differentiate. The transplanted cells may form a mixture of differentiated cell types and tumor cells. The specific differentiated cell types of interest can be selected and purified away from the tumor cells by use of lineage specific markers, e.g., by fluorescent activated cell sorting (FACS) or other sorting method, e.g., magnetic activated cell sorting (MACS). The differentiated cells may then be transplanted into a subject (e.g., an autologous subject, HLA-matched subject) to treat a disease or condition. The disease or condition may be a hematopoietic disorder, an endocrine deficiency, degenerative neurologic disorder, hair loss, or other disease or condition described herein.

Production of EpCAM and Composition Thereof

For the purposes of inducing pluripotency, a composition of EpCAM protein may be provided. Where EpCAM is produced using recombinant techniques, the EpCAM proteins may be produced as an intracellular protein or as an secreted protein, using any suitable construct and any suitable host cell, which can be a prokaryotic or eukaryotic cell, such as a bacterial (e.g. *E. coli*) or a yeast host cell, respectively.

Other examples of eukaryotic cells that may be used as host cells include insect cells, mammalian cells, and/or plant cells. Where mammalian host cells are used, the cells may include one or more of the following: human cells (e.g. Hela, 293, H9 and Jurkat cells); mouse cells (e.g., NIH3T3, L cells, and C127 cells); primate cells (e.g. Cos 1, Cos 7 and CV1) and hamster cells (e.g., Chinese hamster ovary (CHO) cells).

A wide range of host-vector systems suitable for the expression of the subject protein may be employed according standard procedures known in the art. See for example, Sambrook et al. 1989 *Current Protocols in Molecular Biology* Cold Spring Harbor Press, New York and Ausubel et al. 1995 *Current Protocols in Molecular Biology*, Eds. Wiley and Sons.

EpCAM polypeptides may be produced recombinantly not only directly, but also as a fusion polypeptide with a heterologous polypeptide, e.g. a polypeptide having a specific cleavage site at the N- or C-terminus of the mature protein or polypeptide. Expression vectors usually contain a selection gene, also termed a selectable marker. This gene encodes a protein necessary for the survival or growth of transformed host cells grown in a selective culture medium.

Where EpCAM polypeptides is generated in a cell based system, the method may involve inserting a nucleic acid (e.g., cDNA or genomic DNA) encoding EpCAM into a replicable vector for expression. Many such vectors are available. The vector components generally include, but are not limited to, one or more of the following: an origin of replication, one or more marker genes, an enhancer element, a promoter, and a transcription termination sequence.

Expression vectors will contain a promoter that is recognized by the host organism and is operably linked to the EpCAM-encoding sequence. Promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native EpCAM promoter sequence and many heterologous promoters may be used to direct expression of a EpCAM. Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself.

Isolation and purification of a protein can be accomplished according to methods known in the art. For example, a protein can be isolated from a lysate of cells genetically modified to express the protein constitutively and/or upon induction, or from a synthetic reaction mixture, by immunoaffinity purification, which generally involves contacting the sample with an antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. EpCAM may contain modifications to facilitate isolation.

EpCAM may be prepared in substantially pure or isolated form (e.g., free from other polypeptides). The protein can present in a composition that is enriched for the polypeptide relative to other components that may be present (e.g., other polypeptides or other host cell components). Purified protein may be provided such that the protein is present in a composition that is substantially free of other expressed proteins, e.g., less than 90%, usually less than 60% and more usually less than 50% of the composition is made up of other expressed proteins.

Where protein transduction is carried out, EpCAM may be provided to the differentiated somatic cells alone in a single composition or in combination with other proteins and/or nucleic acids. Additional proteins and/or nucleic acids that enhance the redifferentiation process of nonpluripotent cells into pluripotent cells. These additional factors may be added to the cells simultaneously or sequentially at different times from EpCAM.

Kits

Kits may be provided to practice methods of the present disclosure. The kit contains EpCAM or EpCAM-encoding nucleic acids and reagents that are sufficient to induce a nonpluripotent cell into iPS. Kits are also provided to differentially identify a pluripotent cell generated by the methods of the present disclosure. Kits may include one or more reagents specific for a pluripotent cell or a combination of markers to identify pluripotent cells, and may further include antibodies specific for EpCAM. The antibodies may be detectably labeled. The kits may also include reagents to isolated and/or maintain iPS cell populations. Tubes, buffers, etc., and instructions for use can also be included.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which are limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention.

Experimental

The expression of EpCAM was profiled by immunofluorescence microscopy, Western blotting, and flow cytometry using an anti-EpCAM monoclonal antibody (MAb) OC98-1. EpCAM was found to be highly and selectively expressed by undifferentiated rather than differentiated hESCs. The protein and transcript level of EpCAM rapidly diminished as soon as hESC had differentiated. This silencing was closely and exclusively associated with the radical transformation of histone modification at the EpCAM promoter. Moreover, the dynamic pattern of lysine 27 trimethylation of histone 3 (H3K27me3) was conferred by the interplay of SUZ12 and JMJD3, both of which were involved in maintaining hESC pluripotency. In addition, chromatin immunoprecipitation (ChIP) analysis elucidated EpCAM's direct regulation of several reprogramming genes, including c-Myc, Oct-4, Nanog, Sox2 and Klf4, which help maintain the sternness of hESCs. The results presented below indicate that EpCAM and its antibody can be used as a stem cell surface marker and useful for generation of induced pluripotent stem (iPS) cells.

Methods

Cell Culture.

Human embryonic stem cell line H9, hES5, HUES3 and HUES6 cells were passaged every 3~4 days enzymatically with 0.25% trypsin/EDTA (Gibco-BRL, Grand Island, N.Y.) and cultured in Dulbecco's modified Eagle's medium (DMEM; Invitrogen, Carlsbad, Calif.) with 10% knockout serum replacer (KOSR; Invitrogen), 2 mM L-glutamine (Gibco), 0.1 mM nonessential amino acids (Invitrogen), 0.05 mM β-mercaptoethanol (Sigma-Aldrich, St. Louis, Mo.), and 10 ng/ml basic fibroblast growth factor-2 (bFGF-2; Invitrogen). Medium was changed daily. H9, hES5, HUES3 and HUES6 cells were cultured on murine embryonic fibroblasts (MEFs) obtained from the American Type Culture Collection (Manassas, Va.) in porcine skin gelatin-coated (Sigma-Aldrich) 6-well dishes. MEFs were cultured in DMEM with 10% fetal calf serum (FCS) under a humidified atmosphere of 95% air and 5% CO2 at 37° C.

Flow Cytometry Analysis.

hESCs and MEF fibroblasts were dissociated with 0.25% trypsin-EDTA (1 mM) (Gibco) for 3 minutes. Cells were washed with FACS buffer (PBS containing 1% FCS) and then incubated for 1 hr at 4° C. in FACS buffer with the corresponding monoclonal antibody (MAb): anti-EpCAM MAb (OC98-1) generated in our lab at dilutions that ranged from 0.0001 to 1 µg/ml, anti-SSEA4 MAb (2 µg/ml; 90231; Chemicon, Temecula, Calif.) and anti-CD29 MAb conjugated to Alexa647 (dilution 1:10; MCA2298A647; Serotec, Oxford, UK). Phycoerythrin-conjugated goat anti-mouse IgG was used as a secondary antibody (dilution 1:250; Jackson Immuno-Research Laboratories, West Grove, Pa.). For cell sorting, primary antibodies were used as the following: anti-EpCAM MAb (OC98-1) at 0.1 µg/ml, anti-SSEA4 MAb conjugated to phycoerythrin (dilution 1:30; FAB/435P; R&D Systems, Minneapolis, Minn.), and anti-CD29 MAb conjugated to Alexa647 (dilution 1:10; MCA2298A647; Serotech). Fluorescein isothiocyanate-conjugated goat anti-mouse IgG was used as a secondary antibody (dilution 1:250; Jackson Immuno-Research Laboratories). Flow-cytometry analysis was performed with a BD FACSCanto II flow cytometer (Becton Dickinson, San Jose, Calif.).

Protein Extraction and Western Blot Analysis.

Cells were lysed in the lysis buffer (150 mM NaCl, 50 mM Tris-HCl [pH 7.4], 1% Nonidet P-40) plus proteinase inhibitor cocktail (Roche, Indianapolis, Ind.). Proteins were electrophoresed on 10% sodium dodecyl sulfate-polyacrylamide gel electrophoresis (SDS-PAGE) and then transferred to a nitrocellulose membrane (Hybond-C Super; Amersham, Little Chalfont, UK). The membranes were incubated with anti-EpCAM (2 µg/ml; OC98-1) or anti-α-tubulin (1:10,000; Sigma-Aldrich) MAbs. HRP-conjugated goat anti-mouse IgG (H+L) (Jackson Immuno-Research Laboratories) was used as the secondary antibody. Bound antibodies were detected using enhanced chemiluminescence reagents (ECL; Amersham).

Immunofluorescence Assay.

hESCs cultured on coverslips were fixed in 2% paraformaldehyde in PBS for 10 min, washed, and then blocked with 1% BSA in PBS for 10 min. Cells were incubated at room temperature with primary antibody anti-EpCAM MAb (1 µg/ml; OC98-1) or anti-Oct-4 MAb (2 µg/ml; sc-5279; Santa Cruz Biotech, Santa Cruz, Calif.) in 1% BSA. After 1 hr incubation, cells were washed and incubated with fluorescein isothiocyanate goat anti-mouse secondary antibody (Jackson ImmunoResearch Laboratories) for another 1 hr at room temperature. Unbound antibodies were removed by three washes in PBS. DAPI was added for cell counterstaining.

RNA Extraction and Quantitative Real-Time RT-PCR.

Total RNAs were prepared from the cell lines using ULTRASPEC RNA isolation reagent (Biotecx Laboratories, Houston, Tex.). cDNAs were reverse-transcribed with oligo (dT) primer (Fermentas, Glen Burnie, Md.) from 4 µg of total RNA using SuperScript III RNase H-reverse transcriptase (Invitrogen) according to the manufacturer's instructions. The forward and reverse primers for PCR are listed in Table S1. Quantitative RT-PCR was performed by using the LightCycler480 System (Roche). The gene expression level of each sample was normalized to the expression level of GAPDH in the same sample using the LightCycler480 software. The ratios of EpCAM/GAPDH, Oct-4/GAPDH, c-Myc/GAPDH, Nanog/GAPDH and Sox2/GAPDH of the H9 cell line and that of Collagen, type III, alpha 1 (COL3A1)/GAPDH of 15-day differentiated H9 were set to 1.0. The other ratio values of each gene were recalculated accordingly. The reactions were performed in triplicate, and standard deviation calculated.

Enzyme-Linked Immunosorbent Assay (ELISA).

96-well plates (Corning Costar, St. Louis, Mo.) were seeded with H9, hES5, HUES3, HUES6 and MEF cells. The plates were washed with PBS and blocked with 1% BSA. Anti-EpCAM MAb (1 µg/ml; OC98-1) was added to the plates of cells and incubated for 1 hr. The plates were then washed with PBS containing 0.1% (wt/vol) Tween-20 (PBST0.1) and incubated with horseradish peroxidase (HRP)-conjugated anti-mouse immunoglobulin G (IgG) (Jackson ImmunoResearch Laboratories) for another hour. After washing, the plates were incubated with substrate solution o-phenylenediamine dihydrochloride (OPD, Sigma, USA). The reaction was stopped by adding 3 N HCl, and the plates were read using a microplate reader at 490 nm.

Genomic DNA Isolation, Bisulfite Modification and MSP.

The CpG methylation status of OPG promoter was evaluated by MSP. The genomic DNA was purified using the Wizard genomic DNA purification kit (Promega, Madison, Wis.). The bisulfite reaction was performed on 500 ng DNA and further subjected to bisulfite modification by EZ DNA methylation kit according to the manufacturer's directions (Zymo Research, Orange, Calif.). The primers used for the MSP amplifications are listed in Supplementary Table S1. PCRs were performed in a thermocycler (Bio-Rad Laboratories, Richmond, Calif.) for 40 cycles at 95° C. for 1 sec, 51° C. for 5 sec, and 72° C. for 25 sec, followed by a final extension at 72° C. for 10 sec to amplify bisulfite-modified DNA.

Bisulfite Sequencing.

Genomic DNA (500 ng) was treated with EZ DNA modification kit (Zymo Research) according to the manufacturer's recommendations. Completely methylated and unmethylated control genomic DNA was purchased from Qiagen (Qiagen Inc., Valencia, Calif.). The promoter regions of EpCAM and Oct-4 genes were amplified by PCR. Primer sequences used for PCR amplification are listed in Table S1. The PCR products were subjected to purification using the QIAquick PCR Purification Kit (Qiagen) following the manufacturer's instructions. The purified PCR products were then subcloned into a TA cloning vector (pGEM-T Easy vector; Promega). Twenty clones (for control DNA) or ten clones of each sample were verified by sequencing with the T7 universal primer.

Chromatin Immunoprecipitation and Quantitative Real-Time PCR.

ChIP assays were carried out on 1×105 H9 and differentiated H9 (H9 Diff.) cells. The protein-DNA complexes were fixed using 1% formaldehyde, and the cross-linking fixation was quenched by adding glycine to a final concentration of 200 mM. The chromatin complexes were then sonicated to an average size of 250 bp MISONIX Sonicator 3000. We used 2.4 µg anti-H3K4me3 (ab8580; Abcam, Cambridge, Mass.), 2.4 µg anti-H3K9K14Ac (06-599; Upstate-Millipore, Charlottesville, Va.), 5 µg anti-H3K27me3 (ab6002; Abcam), 5 µg anti-H3K9me3 (07-442; Upstate), 2 µg anti-SUZ12 (ab12073; Abcam), 4 µg anti-JMJD3 (AP1022a; Abgent, San Diego, Calif.), and 4 µg anti-EpICD (A-20; Santa Cruz Biotech) for immunoprecipitations, which were performed at 4° C. with indicated antibodies by incubation with Protein A beads (Invitrogen) for 2 hrs. The immunocomplexes were further incubated with chromatin for another 2 hrs. The bound fraction was isolated by Protein A beads according to the manufacturer's instructions, and the immunocomplexes were subsequently subjected to reverse crosslinking. The immunoprecipitated DNA was recovered by PCR purification kit (Qiagen) according to the manufacturer's instructions, and target DNA amount was detected by real-time PCR using the LightCycler480 System (Roche). The amplification primers are listed in Table S1. For each sample, PCR analysis was performed in triplicate, and the bound fraction was compared with input DNA of 1×104 cells. The results reported as the ratio of immunoprecipitated DNA to input DNA (IP/Input). To obtain relative occupancy values, the IP/Input was further normalized to the level observed at a control region, HBB (H3K4me3, H3K9K14Ac and SUZ12) or GAPDH (H3K27me3, H3K9me3, JMJD3 and EpCAM), which was defined as 1.0.

Statistics.

Statistical analyses were tested using the unpaired Student's t tests as appropriate. P<0.05 was considered significant.

TABLE S1

Primers Used for Cloning, Quantitative PCR/RT-PCR

| Gene | Genebank | Forward Primer | Reverse Primer |
|---|---|---|---|
| Quantitative RT-PCR primers | | | |
| EpCAM | NM_002354 | AACAGACAAGGACACTGAAATAAC (SEQ ID NO: 1) | CCGCAAACTTTTACTATCATAAGG (SEQ ID NO: 2) |
| Oct-4 | NM_002701 | GGAGAGCAACTCCGATGG (SEQ ID NO: 3) | TTGATGTCCTGGGACTCCTC (SEQ ID NO: 4) |
| COL3A1 | NM_000090 | TCCGGGTGAGAAAGGTGA (SEQ ID NO: 5) | GCAGGTCCAGAACCTCCAG (SEQ ID NO: 6) |
| c-Myc | NM_002467 | AAACACAAACTTGAACAGCTAC (SEQ ID NO: 7) | ATTTGAGGCAGTTTACATTATGG (SEQ ID NO: 8) |
| Nanog | NM_024865 | ATGCCTCACACGGAGACTGT (SEQ ID NO: 9) | AGGGCTGTCCTGAATAAGCA (SEQ ID NO: 10) |
| Sox2 | NM_003106 | TATTTGAATCAGTCTGCCGAG (SEQ ID NO: 11) | ATGTACCTGTTATAAGGATGATATTAGT (SEQ ID NO: 12) |
| Klf4 | NM_004235 | ACCAGGCACTACCGTAAACACA (SEQ ID NO: 13) | GGTCCGACCTGGAAAATGCT (SEQ ID NO: 14) |
| GAPDH | NM_002046 | CTTCACCACCATGGAGGAGGC (SEQ ID NO: 15) | GGCATGGACTGTGGTCATGAG (SEQ ID NO: 16) |
| ChIP primers | | | |
| EpCAM (−630 to −550) | NM_002354 | ACATCTTCAAGTGCTAGAAATGC (SEQ ID NO: 17) | GAAATCTTGGCTCTCTTGGG (SEQ ID NO: 18) |
| EpCAM (−354 to −273) | NM_002354 | CCATTCTTCAAGGCTTCAGAG (SEQ ID NO: 19) | GGCGTTAGGGATCTTTGGT (SEQ ID NO: 20) |
| EpCAM (+426 to +539) | NM_002354 | CCTCACTTCGCAGCTTTG (SEQ ID NO: 21) | GCCGCAGGAAACCTGGA (SEQ ID NO: 22) |
| EpCAM (+835 to +967) | NM_002354 | GCTTATTGTAGGGAACGCAG (SEQ ID NO: 23) | CGACAGAGCAAGACTCAG (SEQ ID NO: 24) |
| c-Myc (−341 to −208) | NM_002467 | GCCTGCGATGATTTATACTCAC (SEQ ID NO: 25) | AAACAGAGTAAGAGAGCCG (SEQ ID NO: 26) |
| c-Myc (+214 to +358) | NM_002467 | CTAGGGTGGAAGAGCCG (SEQ ID NO: 27) | GCTGCTATGGGCAAAGTT (SEQ ID NO: 28) |

TABLE S1-continued

Primers Used for Cloning, Quantitative PCR/RT-PCR

| Gene | Genebank | Forward Primer | Reverse Primer |
|---|---|---|---|
| Oct-4 (−173 to −96) | NM_002701 | CAGTTGTGTCTCCCGGTTTT (SEQ ID NO: 29) | CAGTTGTGTCTCCCGGTTTT (SEQ ID NO: 29) |
| Oct-4 (−2613 to −2396) | NM_002701 | GGGGAACCTGGAGGATGGCAAG CTGAGAAA (SEQ ID NO: 30) | GGCCTGGTGGGGGTGGGAGG AACAT (SEQ ID NO: 31) |
| KRT1 | NM_006121 | GTGGCACAGAGTTTAGTGA (SEQ ID NO: 32) | TGGGTACTCTTGCACTTG (SEQ ID NO: 33) |
| Nanog | NM_024865 | TCTTCAGGTTCTGTTGCTCG (SEQ ID NO: 34) | GTTAATCCCGTCTACCAGTCTC (SEQ ID NO: 35) |
| Sox2 | NM_003106 | GGATAACATTGTACTGGGAAG GGACA (SEQ ID NO: 36) | CAAAGTTTCTTTTATTCGTATGT GTGAGCA (SEQ ID NO: 37) |
| Klf4 | NM_004235 | GGAAAGGAGAGTGCGTG (SEQ ID NO: 38) | CACTGCCTGTAATATTTGATGAC TAA (SEQ ID NO: 39) |
| HBB | NM_000518 | ATCTGAGCCAAGTAGAAGACC TTTTC (SEQ ID NO: 40) | TCTGCCTGGACTAATCTGCAAG (SEQ ID NO: 41) |
| GAPDH | NM_002046 | TCCAAGCGTGTAAGGGT (SEQ ID NO: 42) | GAAGGGACTGAGATTGGC (SEQ ID NO: 43) |
| MSP primers | | | |
| EpCAM-Methylated | NM_002354 | TTTAACGTCGTTATGGAGACGA (SEQ ID NO: 44) | GCTAATACTCGTTAATAAATCAC CG (SEQ ID NO: 45) |
| EpCAM-Unmethylated | NM_002354 | TTTAATGTTGTTATGGAGATGA (SEQ ID NO: 46) | ACCACTAATACTCATTAATAAAT CACCAC (SEQ ID NO: 47) |
| Bisulfite sequencing primers | | | |
| EpCAM | NM_002354 | AAGGAAGTTTTAGTATAGAATT TTTAAAT (SEQ ID NO: 48) | AAAAAAATAAATAAACTCCCCT CC (SEQ ID NO: 49) |
| Oct-4 | NM_002701 | ATTTGTTTTTTGGGTAGTTAAA GGT (SEQ ID NO: 50) | CCAACTATCTTCATCTTAATAA CATCC (SEQ ID NO: 51) |

Example 1

EpCAM is Selectively Expressed in hESCs

Figure 1:
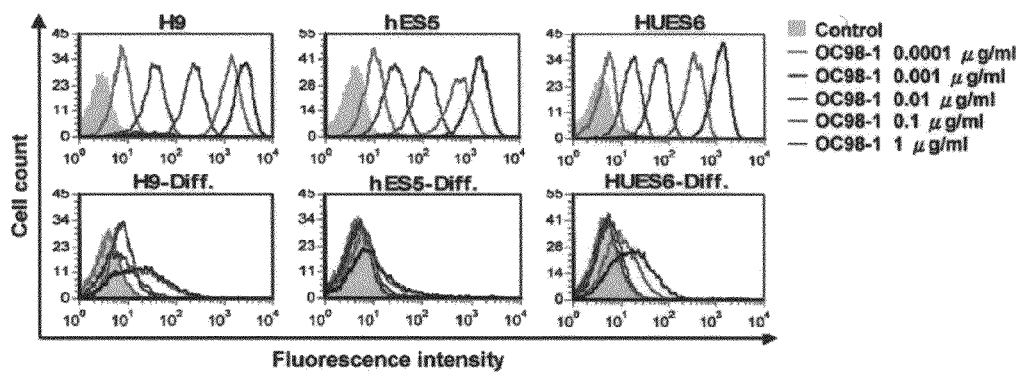
FIG. 1. EpCAM is selectively expressed by hESCs. A: Dose-dependent increase in relative fluorescence intensity was associated with increasing the concentration of anti-EpCAM MAb (OC98-1) against the cell surface of undifferentiated hESCs (top; H9, hES5 and HUES6). Only basal level of EpCAM binding to differentiated hESCs (H9-Diff., hES5-Diff. and HUES6-Diff.) was seen in the bottom. B: Expression of the EpCAM protein in undifferentiated and differentiated hESCs. Lysates from various hESCs cell lines were analyzed by Western blot analysis with the anti-EpCAM and anti-α tubulin MAb. α-tubulin was used as internal controls. C: Immunofluorescent analysis of EpCAM (i and iii) and Oct-4 protein (ii and iv) expression in undifferentiated H9 (i and ii) and in differentiated H9 (iii and iv) cells. Nuclei were counter-stained with DAPI (blue). H9 cells staining for Oct-4 manifested that these hESCs maintained undifferentiated state. EpCAM expression was correlated to that of Oct-4 in undifferentiated H9 (i and ii). hESC differentiation was associated with loss expression of both EpCAM and Oct-4 (iii and iv).
Figure 1:
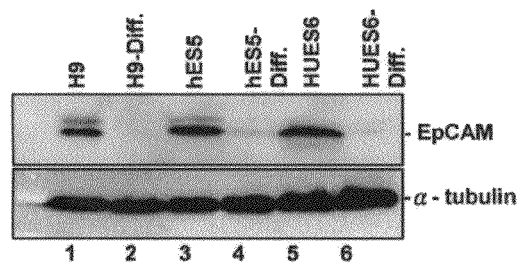
Figure 1:
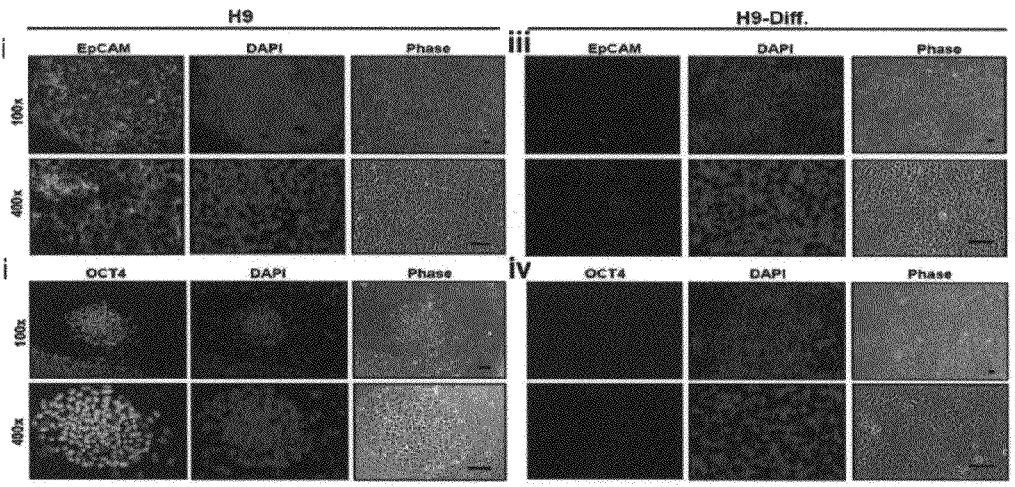

EpCAM has been previously identified as differentially expressed in hepatic stem cells (Schmelzer E et al. (2007) *J. Exp. Med.* 204:1973-1987). To determine whether hESCs expressed EpCAM, we analyzed the cell surface expression of EpCAM protein using fluorescent flow cytometry in undifferentiated hESCs and 30-day differentiated hESCs using our MAb OC98-1 to recognize the extracellular portion of EpCAM (FIG. 1A). We found that the undifferentiated H9, hES5, and HUES6 ES cells cultured on irradiated murine embryonic fibroblasts (MEF, feeder layer) expressed cell surface EpCAM in a dose-dependent binding intensity proportionate to OC98-1 concentration (concentrations ranging from 0.0001 to 1 μg/ml); this molecule was absent from most of the differentiated counterparts (FIG. 1A). SSEA4 labeling in undifferentiated and differentiated hESCs served as experimental control (FIG. 8). In our Western blot analysis, we found EpCAM to be strongly detected in undifferentiated H9, hES5, and HUES6 ES cells but absent in hESCs after differentiation (FIG. 1B), indicating EpCAM was expressed in undifferentiated hESCs exclusively.

Undifferentiated H9, hES5, and HUES6 colonies were subjected to spontaneous differentiation by culture in 10% FCS-containing media for 30 days. Immunofluorescent microscopy was used to detect the expression of EpCAM and Oct-4 proteins for both undifferentiated and differentiated hESCs (FIG. 1C). Differentiated cells lost Oct-4 protein expression, indicating that spontaneous differentiation had occurred. An absence of EpCAM protein correlated with loss of Oct-4. Examination of EpCAM proteins on H9, hES5, and HUES6 showed selective expression of this molecule in hESCs, suggesting EpCAM may be used as a surface marker for hESCs.

Example 2 hESC Differentiation is Associated with a Loss of EpCAM Expression

EpCAM protein expression was assessed in undifferentiated and differentiated H9 cells by measuring the amount of EpCAM on the surface of cells by flow cytometry (FIG. 2A). Undifferentiated H9 cells expressed cell surface EpCAM on 98% of the population (FIG. 2A, EpCAM), while SSEA4, a known hESC surface antigen, was expressed on most (99%) of the cells (FIG. 2A, SSEA4). At day 5 following induction of differentiation of the cells, a fractional proportion of the population (~14%) lacked cell surface EpCAM (86%; FIG. 2A, EpCAM, day 5), though they retained expression of SSEA4 protein (98%; FIG. 2A, SSEA4, day 5). At day 10 following induction of differentiation, we found a gradual reduction of EpCAM (~63%; FIG. 2A, EpCAM, day 10) as well as SSEA4 (~70%; FIG. 2A, SSEA4, day 10) in these cells. At fifteen days, a significant proportion of the cells were found to have low levels of cell surface EpCAM protein (~21%; FIG. 2A, EpCAM, day 15) and SSEA4 protein (~27%; FIG. 2A, SSEA4, day 15).

Transcript expression in the undifferentiated and differentiated H9 populations was analyzed by Q-RT-PCR (FIG. 2B). EpCAM transcripts were detected from undifferentiated H9 cells and at day 5 differentiation, and were rapidly down-regulated at day 10 and at day 15. Oct-4, which is expressed in undifferentiated hESCs, was abundantly detected in undifferentiated H9, with levels decreasing at day 5 and absent at day 10 and day 15. In contrast, COL3A1 transcripts, which are expressed in differentiated cells [34], were found to be absent in undifferentiated H9 but present in differentiated cells at all examination time points (days 5 to 15). Together, these data suggest a close association between hESC differentiation and loss of expression of EpCAM.

Example 3

Specificity of EpCAM Surface Expression in hESCs

Figure 3:
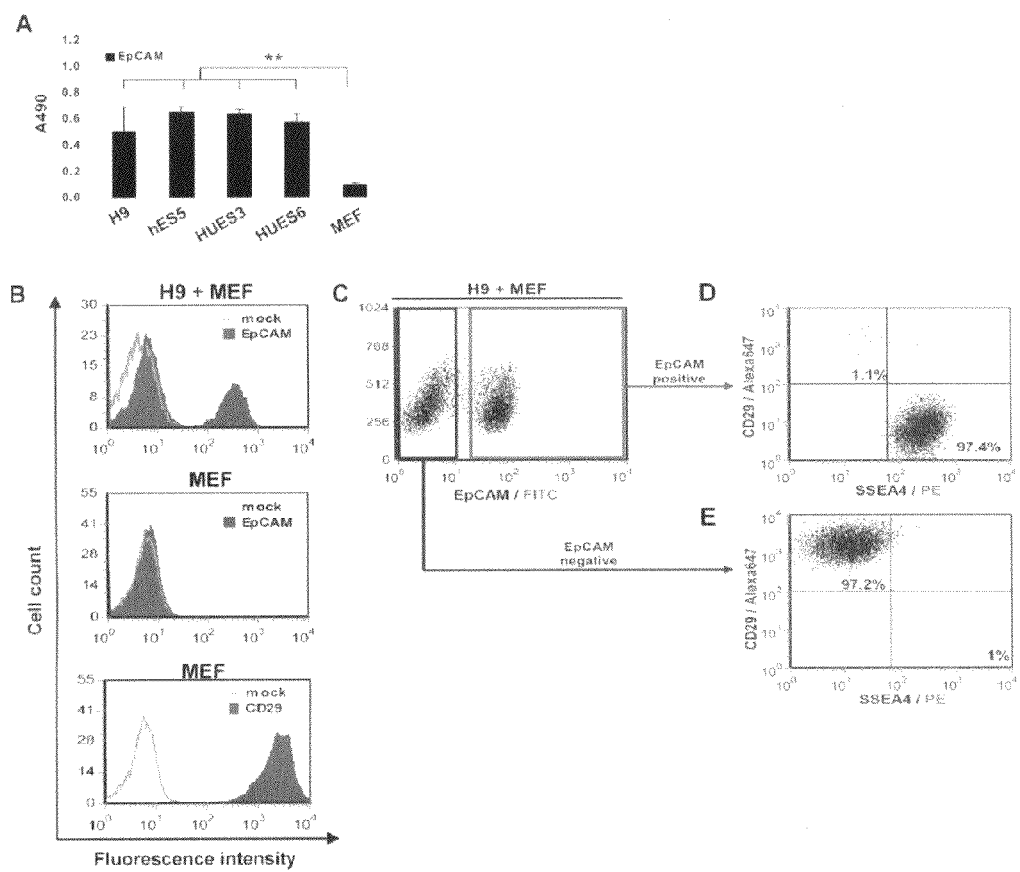
FIG. 3. Cell surface EpCAM expression and isolation of hESCs. A: Cell surface EpCAM protein expression by undifferentiated hESCs (H9, hES5, HUES3 and HUES6) and feeder MEF by ELISA analysis using an anti-EpCAM MAb (**, P<0.01). B: Flow cytometry analysis of EpCAM on H9 hESCs co-cultured with MEF (top) and MEF alone (middle), and analysis of CD29 on MEF alone (bottom). C: Analysis of cell surface expression of EpCAM on H9 cells co-cultured with MEF by fluorescent flow cytometry. D and E: Double labeling of EpCAM positive (D) and EpCAM negative (E) population with anti-SSEA4 and anti-CD29 antibodies on undifferentiated H9 cells co-cultured with MEF.

We next investigated whether EpCAM could be used reliably as a marker to identify, isolate, and qualify hESCs in vitro. As shown in FIG. 3A, the results of our ELISA, we found a significant relationship between EpCAM level and hESCs, including undifferentiated H9, hES5, HUES3 and HUES6 cells, but not MEFs. Using flow cytometry, we further demonstrated that EpCAM could discriminate hESCs from MEFs in primary H9/MEF co-cultures (FIG. 3B). MEFs exhibited CD29 positive staining, which was used as a marker for fibroblast identity (FIG. 3B, bottom).

To find out whether the OC98-1 was able to distinguish between two populations of hESCs cultured on MEFs, we used flow-cytometry to analyze EpCAM expression profile on hESCs/MEFs co-cultures. There were two main cell populations, EpCAM+ and EpCAM− (FIG. 3C). When we double stained these two populations with SSEA4 and CD29, we found SSEA4 to be expressed in the hESC EpCAM+ population (97.4%; FIG. 3D), but not in the fibroblast EpCAM−CD29+ population (97.2%; FIG. 3E). These finding show that EpCAM labeling can be used to separate hESCs from fibroblasts and obtain pure hESC populations.

Example 4

EpCAM Methylation Status in Undifferentiated and Differentiated hESCs

Figure 2:
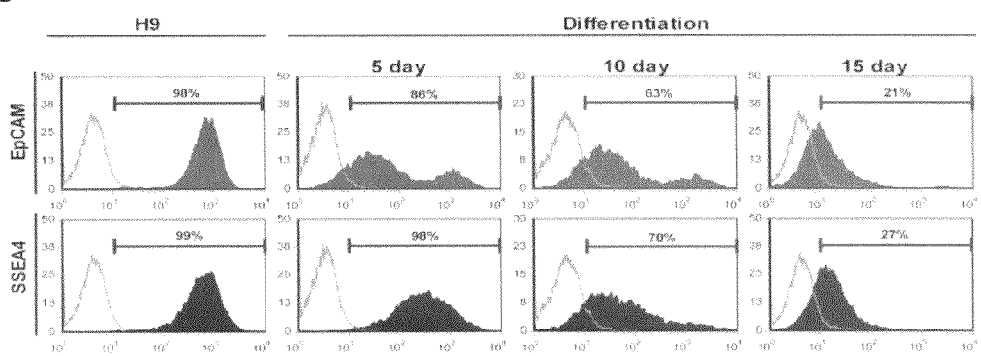
FIG. 2. Human ES cell differentiation was associated with loss of EpCAM. A: Cell surface EpCAM expression histogram was assessed in undifferentiated H9 cells (left panel) and H9 cells differentiated for 5, 10 and 15 day by fluorescent flow cytometry. EpCAM or SSEA4 was closed population, and secondary antibody only was open population. Viable cells were gated using forward and side scatter and the data represents cells from this population. B: Q-RT-PCR analysis of EpCAM, Oct-4, and COL3A1 transcript expression was assessed in undifferentiated H9 cells and in H9 cells differentiated for 5, 10, and 15 days as described above. GAPDH expression was used to normalize the variability in each template loading.
Figure 2:
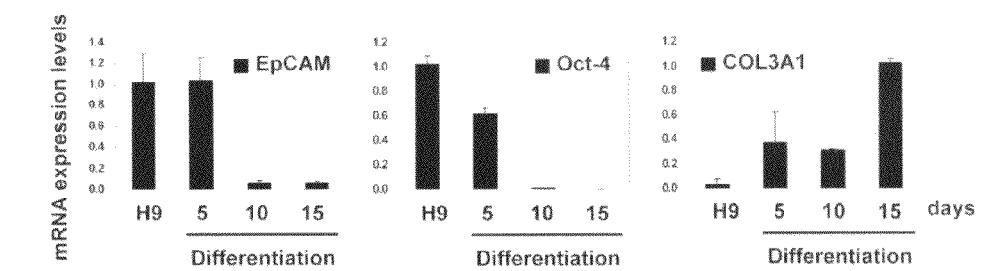
Figure 4:
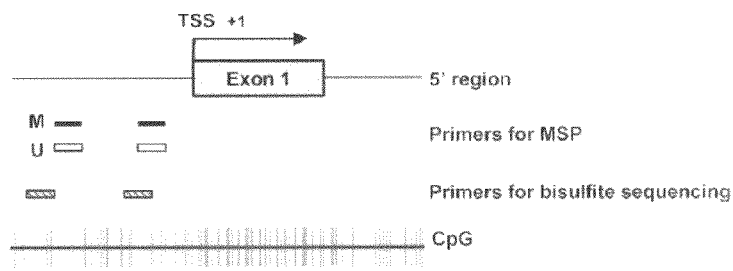
FIG. 4. Methylation status of EpCAM promoter regions in undifferentiated and differentiated hESCs. A: Schematic representation of the EpCAM gene promoter region. Primers for MSP and bisulfite sequencing used in the study are indicated. B: MSP analysis of the EpCAM gene promoter region in undifferentiated and differentiated H9 cells. The PCR-products labeled M (methylated) were generated by methylation-specific primers, and those labeled U (unmethylated) were generated by primers specific for unmethylated DNA. C: Mapping the methylation status of the CpG islands in the promoter region of the EpCAM gene by bisulfite sequencing. Each row of squares represents a single plasmid cloned and sequenced from PCR products generated from amplification of bisulfite-treated DNA. Open squares represent unmethylated cytosines; filled squares represent methylated cytosines. Most CpGs in the promoter region in both undifferentiated and differentiated H9 cells were unmethylated.
Figure 4:
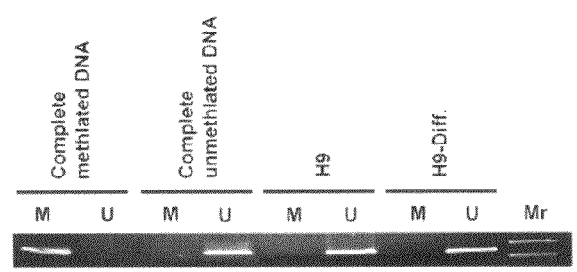
Figure 4:
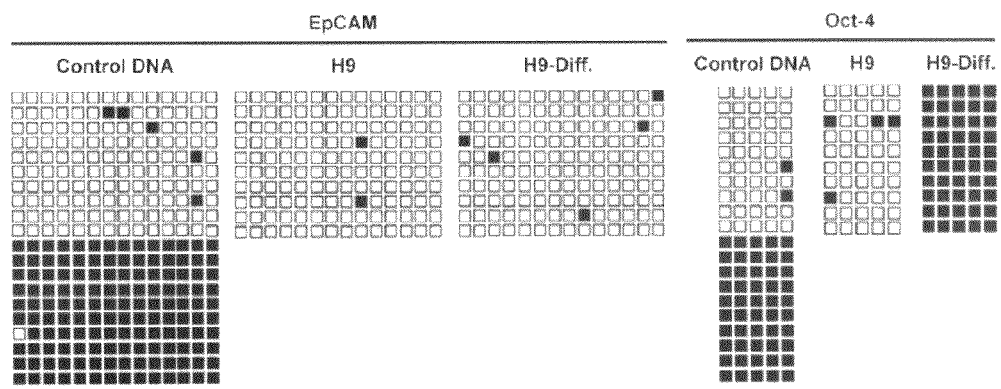

The EpCAM gene expression was completely silenced during hESCs undergoing differentiation (FIG. 2). To determine whether EpCAM expression correlated with DNA methylation, we examined the methylation status of EpCAM promoter regions in both undifferentiated and differentiated hESCs. FIG. 4A depicts the gene structure and CpG contents encompassed the EpCAM promoter region. Primers for MSP and bisulfite sequencing were designed to target the 5' flanking region of the EpCAM promoter. MSP assays were performed to determine the methylation status of EpCAM for both undifferentiated and differentiated hESCs. We used commercial available completely methylated and completely unmethylated DNAs as positive controls validating the primers' property in this experiment. As shown in FIG. 4B, both undifferentiated and differentiated H9 cells revealed abundant amounts of unmethylated PCR product, whereas in differentiated H9 cells there were trace amounts of methylated PCR product.

To further ensure the reliability of this finding, we used bisulfite sequencing to evaluate the methylation statuses of CpG in the promoter region of EpCAM. By clone sequencing analysis, we found 98% of the CpG sites of the undifferentiated H9 clones and 96% of those of the differentiated H9 ones to be unmethylated (FIG. 4C). We included a positive control, Oct-4, which is unmethylated in ES cells and methylated in differentiated cells [27] (FIG. 4C). As expected, H9 hESCs were predominantly unmethylated at the Oct-4 promoter, while prominent methylation as this locus was found in differentiated H9 cells, a finding consistent with previous studies of transcriptional silencing in the differentiated cells [27]. These results indicate that EpCAM silencing during hESC differentiation may not be due to changes in the methylation status of the EpCAM promoter in these cells.

Example 5

Histone Modification of EpCAM Promoter Region in Undifferentiated and Differentiated hESCs Covalent histone tail modifications of histone 3, including acetylation or methylation, regulate these different states of chromatin configuration and gene transcription. To address whether there is an association between the expression of EpCAM expression and chromatin architecture, we determined the profile of histone modification of EpCAM promoter vicinity in undifferentiated and differentiated H9 cells. To do this, we performed ChIP assays on four regions of EpCAM promoter: the upstream distal (−630~−550) and proximal (−354~−273) and the downstream proximal (+426~+539) and distal (+835~+967) relative to transcription start site (TSS). We also explored the histone marks of lysine 4 trimethylation of histone 3 (H3K4me3), lysine 9/14 acetylation of histone 3 (H3K9K14Ac), lysine 27 trimethylation of histone 3 (H3K27me3), and lysine 9 trimethylation of histone 3 (H3K9me3).

H3K4me3 has been positively correlated with gene expression [37]. As shown in FIG. 5A, the kinetics of H3K4me3, there was an increase of occupancy in undifferentiated H9 cells expressing EpCAM in both proximal and distal regions downstream of TSS, but no significant alterations between these two cells in proximal and distal regions upstream of TSS. There was a significant association between Oct-4, which was expressed in undifferentiated hESCs, and H3K4me3 in the promoter region (FIG. 5A). H3K9K14Ac association has been found to be enriched at 5' end of active genes and has been strongly correlated with H3K4me3 [38]. In EpCAM-positive undifferentiated H9 cells, the acetylation level of H3K9K14 was high in both proximal and distal downstream regions of TSS, as was observed in H3K4me3 (FIG. 5B).

Previous studies have suggested that there is a correlation between H3K27me3 and gene repression (Barski A et al. (2007) *Cell* 129:823-837). Indeed, our study found H3K27me3 signals to be elevated at all upstream and downstream regions of silent promoters of differentiated H9 cells that did not express EpCAM (FIG. 5C). Methylation of lysine 9 of histone 3 is known to facilitate formation of heterochromatin, and elevated levels of H3K9me3 at promoter sequences have been associated with suppression of gene expression. Our study found greater increases in H3K9me3 on all four promoter regions in differentiated H9 than in undifferentiated H9 cells (FIG. 5D). This profiling of histone modification by ChIP assay suggests that chromatin remodeling in the 5' flanking region of the EpCAM promoter may be responsible for EpCAM gene regulation.

Example 6

SUZ12 and JMJD3 are Required for Bi-Directional Regulation of H3K27me3 in hESCs

Figure 5:
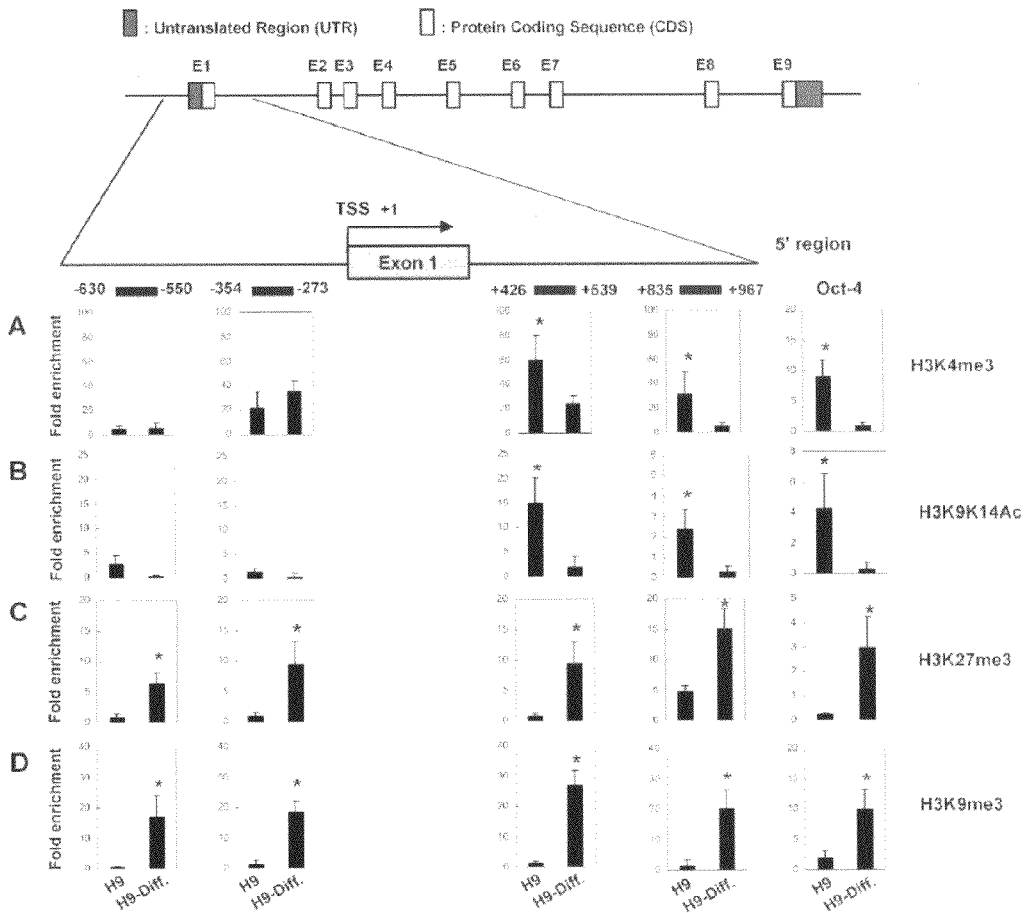
FIG. 5. Histone modification at EpCAM promoter in undifferentiated and differentiated hESCs. Top: Schematic representation of the EpCAM gene promoter region, which spanned positions −630 to +967 with respect to the TSS. The ChIP primers used in the study are indicated by horizontal lines. A, B, C and D: A combination of ChIP and Q-PCR analyses showing quantitative occupancy of H3K4me3 (A), H3K9K14Ac (B), H3K27me3 (C) and H3K9me3 (D) to EpCAM and Oct-4 promoter in undifferentiated and differentiated H9 cells. Oct-4 was used as a positive control for histone modification binding. In ChIP analyses, H3K4me3 and H3K9K14Ac enrichment were observed in undifferentiated H9 cells at the downstream of TSS, while H3K27me3 and H3K9me3 occupancy were detected in differentiated H9 cells at both the upstream and downstream of TSS (*, P<0.05).

In hESCs, EpCAM was marked by a chromatin signature that was dynamically regulated during differentiation (FIG. 5). Hence, the observation that SUZ12 and JMJD3 are recruited to their promoters prompted us to assess the dynamic profile of H3K27 methylation at the TSS of EpCAM during stem cell differentiation. To test whether SUZ12 conferred the methylation of H3K27 of EpCAM, we performed ChIP of both undifferentiated and differentiated H9 cells. Remarkably, we detected higher SUZ12 signals in differentiated H9 than in undifferentiated H9 both upstream and downstream of EpCAM promoter (FIG. 6A), and these results were strongly mirrored by H3K27me3 occupancy. These results suggest that EpCAM is controlled by PRC2 complex, the major histone methyl transferase responsible for H3K27me3. We compared this with a parallel control—KRT1 (FIG. 6), an epidermal differentiation genes, which is subjected to H3K27me3/SUZ12/JMJD3 regulation.

Conversely, at the downstream of EpCAM TSS of undifferentiated H9 cells, both proximal and distal promoter regions, we found a corresponding rise in JMJD3 binding (FIG. 6B) which coincided with the reduction of H3K27me3 (FIG. 5C) suggesting a direct causal relationship between JMJD3 recruitment and H3K27 demethylation. These findings indicate that EpCAM expression in hESC is maintained by the loss of H3K27me3 and SUZ12 as well as the increase in JMJD3 on the promoters of EpCAM gene.

Example 7

EpCAM is Involved in ES Cell Maintenance Through its Influence on c-Myc, Oct-4, Nanog, Sox2 and Klf4

It is of biological significance to study the function of EpCAM at the molecular level in ES cells. In order to correlate EpCAM with its early response molecule c-Myc and other possible downstream targets such as Oct-4, Nanog, Sox2 and Klf4, we examined expression of these genes using Q-RT-PCR. We found that all of the four genes were highly expressed in hESCs but collapsed after hESC differentiation was induced (FIGS. 2B and 7A). The expression of these genes remained repressed during differentiation at all observation time points (days 5-15; FIGS. 2B and 7A). To directly determine whether EpCAM regulated these genes, we performed ChIP assays in both undifferentiated H9 (H9) and differentiated H9 (H9-Diff.) cells with the EpICD antibody. There was a three times greater increase of EpICD binding in undifferentiated H9 than in H9-Diff. cells at the proximal upstream region of TSS of the c-Myc promoter. In contrast, there was no significant EpICD binding to the control downstream Exon 1 of the c-Myc in either cells (FIG. 7B).

It was interesting to observe that there was EpICD binding to Oct-4 (distal upstream region), Nanog (upstream region), Sox2 (downstream region) and Klf4 (upstream region) promoters as well, possibly suggesting that that EpCAM modulates ES phenotype through promoting the expression of these downstream targets (FIG. 7C). Based on these findings, we propose that EpCAM expression in hESCs is regulated by an epigenetic mechanism, and EpCAM activates gene expression of c-Myc, Oct-4, Nanog, Sox2 and Klf4 through transducing signal to nucleus by EpICD, resulting in self-renewal and the maintenance of pluripotency in ES cells (FIG. 7D).

Example 8

Overexpression of EpCAM Enhances Reprogramming Efficiency in MEFs

Material and Methods

Mouse iPSCs were generated using lentiviruses produced by TetO-FUW-mOSKM (Addgene, Cambridge, Mass., http://www.addgene.org) that contained mouse Oct4, Sox2, Klf4 and c-Myc cDNAs in one plasmid and TetO-FUW-EpCAM, and simultaneously by FUW-M2rtTA, (Addgene). 293T cells were transfected with these two lentiviral vectors accompanied with pCMVΔ8.9 and pCMV-VSVG (Addgene) using FuGENE® 6 transfection reagent (Roche, Swiss, http://www.roche.com). Viral supernatant fractions were harvested at 60 hours and 84 hours after transfection and filtered through a 0.45 μm filter (Millipore). MEFs were then infected with two rounds of lentiviruses 24 hours apart and incubated with viruses for another 24 hours before the medium was changed to regular MEF medium. After four days, cells were transferred onto feeder cells and the medium was replaced with regular mESC medium. Doxycycline (2 μg/ml) was added 24 hours later to induce the expression of 4 reprogramming factors. iPSC colonies were subjected to in vitro and in vivo characterization, or manually picked and expanded 20 days after viral transduction.

Results

To test whether over-expression of EpCAM proteins can promote Oct, Sox-2, Klf4 and c-Myc (OSKM)-mediated reprogramming, we transduced MEFs with inducible lentiviruses encoding EpCAM in the presence of OSKM (FIG. 9) and the reprogramming efficiency was compared by various assays at day 21 after doxycycline induction. Q-RT-PCR analysis showed that transient overexpression of EpCAM could significantly increase the expression level of endogenous Nanog, Oct4, and Sox2 FIG. 9b); and a significant increased in the numbers of AP-positive and Nanog-positive colonies (FIG. 9c).

Discussion

Figure 6:
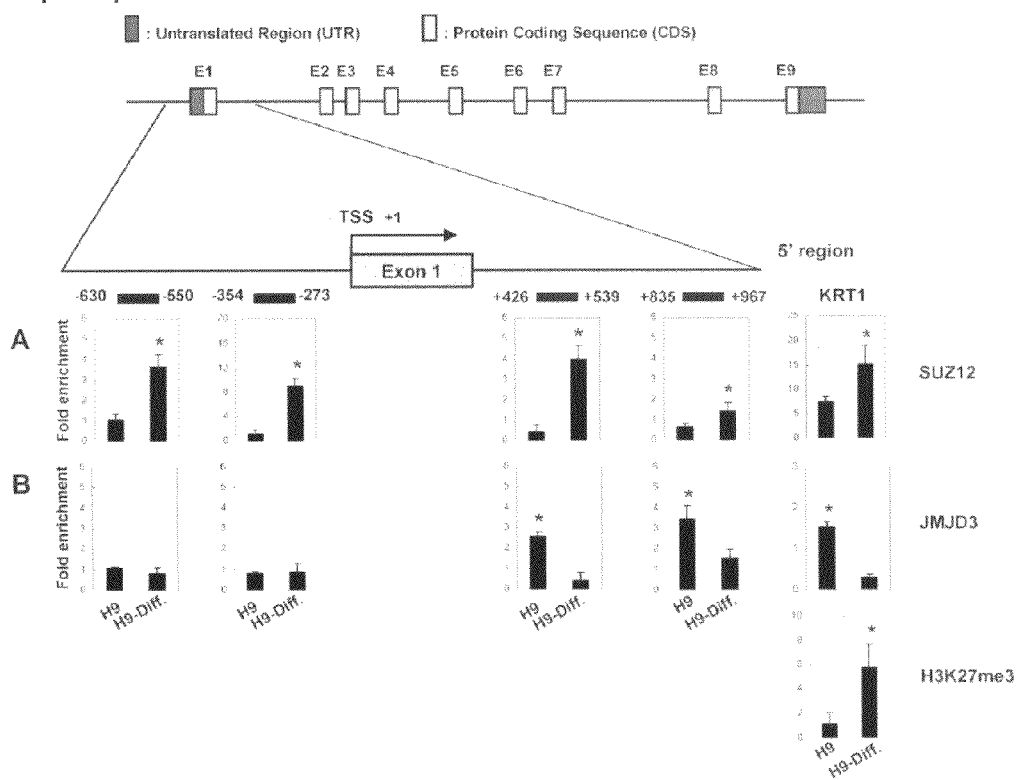
FIG. 6. Recruitment of chromatin modifier SUZ12 and JMJD3 to EpCAM promoter in undifferentiated and differentiated hESCs. Top: Schematic representation of the EpCAM promoter locus, which spanned positions −630 to +967 with respect to the TSS. The ChIP primers used in the study are indicated by horizontal lines. A and B: Chromatin samples were immunoprecipitated with anti-SUZ12 antibody (A) or anti-JMJD3 antibody (B), and enrichment of the EpCAM and KRT1 promoter was quantitated by Q-PCR. KRT1 was used as a control for SUZ12/JMJD3/H3K27me3 binding. By ChIP measurement, the association of SUZ12 with the EpCAM promoter was elevated at both the upstream and downstream of TSS in differentiated H9 cells. In contrast, quantification of the intensities of JMJD3 binding was increased at the downstream of TSS in undifferentiated H9 cells (*, P<0.05).

The recent successful use of somatic cells that can be directly reprogrammed into pluripotency and self-renewal stem cells has opened a new means of investigating basic biology, developmental biology, and regenerative medicine. Ectopic transduction of terminally differentiated fibroblasts with the original four reprogramming transcription factors Oct4, Sox2, Klf4 and c-Myc results in iPS cells formation morphologically and genetically. These four factors play a pivotal role in ES cell self-renewal and maintenance of pluripotency. However, until this study it was unknown what was mutually regulating these four genes. This study found that EpICD could directly bind to the promoters of these four genes (FIG. 7) and control the up-regulation of these genes in undifferentiated hESCs (FIG. 7). EpCAM expression in undifferentiated hESCs occurred through epigenetic regulation (FIGS. 5 and 6). Based on these findings, we propose that maintenance of sternness by these four genes is controlled by the expression of EpCAM which collaborates with these four factors to maintain self-renewal and pluripotency in ES cells.

The expression of EpCAM has been used to recognize hepatic stem cells in fetal, postnatal and adult humans and is thought to be useful in the selection of cancer-initiating cells.

Our study found EpCAM to be exclusively expressed in hESCs (FIGS. 1 and 3) and its expression to be correlated with the expression of Oct-4 (FIGS. 1 and 2), a known stem cell marker. This finding suggests that cell surface expression property of EpCAM can be used to purify and enrich hESCs effectively, and it can be used as a surrogate for Oct-4 or potentially other hESC markers to simplify and improve the isolation and purity of hESC.

Rigorous hESC isolation is a complicated process requiring various combinations of multiple cell surface markers. Nevertheless, many of the stem cell markers used nowadays cannot be used specifically on hESCs. For example, peanut agglutinin is only applicable as a cell surface marker in murine hematopoietic stem cells and human neural stem cells (Rietze R L et al. (2001) *Nature* 412:736-739), and CD29 expression only can be used as a stem-cell marker in murine skin or liver (Dan Y Y et al. (2006) *Proc Natl Acad Sci USA* 103:9912-9917; Shackleton M et al. (2006) *Nature* 439:84-88). CD133 (prominin-1) has recently emerged as a major somatic stem cell or progenitor marker (Huttner H B et al. (2008) *Stem Cells* 26:698-705). Thus, there is a need to expand the current repertoire of hESC markers to enable hESC studies. Recognition by hESC-selective cell surface molecules is required in order to specifically isolate pure hESCs. Particularly the combination of viable markers has made it possible to separate multiple hESC populations at each distinct differentiation stage and yielded important insights on stem cell differentiation. Because EpCAM is not expressed by differentiated cells, this molecule is likely exerted at the stem or multipotent progenitor cell stage.

The results of studies over the past few years have suggested that epigenetic mechanisms play a key role in these fundamental processes of self-renewal, maintenance of pluripotency, and lineage specification. For example, pluripotency-associated genes, such as Oct4 and Nanog, are stably silenced upon cell differentiation through epigenetic mechanisms (Feldman N et al. (2006) *Nat Cell Biol* 8:188-194). Non-transcribed genes in ESCs are repressed by the PcG in mice and humans with the promoters of these genes enriched with repressive histone H3K27 trimethylation. Our investigation on the epigenetic regulations of EpCAM expression during differentiation indicated that the expression of EpCAM was not regulated by DNA methylation (FIG. 4), which would lead to permanent silencing of the gene. Instead, we found that during differentiation, there is a drastic reduction in histone active markers, such as H3K4 trimethylation and H3K9 acetylation, and clear enhancement of repressive markers H3K9 and H3K27 trimethylation at the promoter of EpCAM (FIG. 5). In addition, EpCAM was not controlled by bivalent chromatin modifications (Azuara V et al. (2006) *Nat Cell Biol* 8:532-538; Bernstein B E et al. (2006) *Cell* 125: 315-326) because H3K4 and H3K27 trimethylation did not coexist at its promoter before or after the differentiation (FIG. 5), indicating that EpCAM does not belong to the category of lineage commitment or cell fate-determination genes (Bernstein B E et al. (2006) *Cell* 125:315-326; Mikkelsen T S et al. (2007) *Nature* 448:553-560). Our findings reflect the fact that EpCAM is virtually reintroduced in mature tissues (Trzpis M et al. (2007) *Am J Pathol* 171:386-395), especially in epithelia cells. Therefore, our results suggest that, to facilitate the dynamic expression pattern of EpCAM during development, the chromatin state of its promoter is elaborately modulated by histone modifying enzymes such as SUZ12 and JMJD3 but not DNA methylation (FIG. 6) in response to hESC differentiation, which sustains the plasticity of EpCAM expression.

Our study found that EpCAM played an intricate role in the regulation of the ES cell state. This may be achieved by modulating the EpCAM's downstream target c-Myc expression, which, as other studies have reported, is involved in governing cell proliferation and de-differentiation. Both c-Myc and EpCAM are controlled by Wnt signaling cascade in which signal transduction by EpICD interacts with β-catenin/Lef-1 in cohort to regulate c-Myc expression. The canonical Wnt signaling pathway has emerged as a critical regulator of ES and hematopoietic-lineage stem cells in other studies. The results of such studies provide a compelling explanation for the high levels of EpCAM in stem or progenitor cells. Through molecular circuitry established around Wnt signaling, EpCAM and c-Myc can collaborate to sustain self-renewal and the pluripotent state of ES cells. Nuclear translocation of EpICD up-regulates c-Myc, Oct-4, Nanog, Sox2 and Klf4 (FIG. 7), indicating EpCAM targeting of these ES cell fate genes may not occur exclusively through Wnt signaling, suggesting that there may be several pathways orchestrating the maintenance of the physical state of ES cells. Further investigations are required to clarify the relationship between Wnt signaling and Oct-4, Nanog, Sox2 and Klf4, as the results of such studies may further our understanding the nature of pluripotency and of self-renewal signals in hESCs.

What is claimed is:

1. A method for producing mammalian induced pluripotent stem cells (iPS cells) the method comprising:
   introducing retroviral vectors comprising a nucleic acid encoding Oct4, Sox2, Klf4, cMyc and epithelial cell adhesion molecule (EpCAM) into an isolated mammalian non-pluripotent cell,
   culturing the cell under conditions that reprogram the non-pluripotent cells into an iPS cell that exhibits self-renewal and pluripotency.

2. The method of claim 1, wherein said mammalian non-pluripotent cell is an adult somatic cell.

3. The method of claim 1, where said mammalian non-pluripotent cell is a human cell.

4. The method of claim 1, wherein said EpCAM is human EpCAM.

5. The method of claim 1, wherein said induced pluripotent stem cell comprise a EpCAM polypeptide at cell surface.

* * * * *

SEQUENCE LISTING

```
<160> NUMBER OF SEQ ID NOS: 51

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
aacagacaag gacactgaaa taac                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic primer
```

```
<400> SEQUENCE: 2
ccgcaaactt ttactatcat aagg                                          24

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
ggagagcaac tccgatgg                                                 18

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ttgatgtcct gggactcctc                                               20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
tccgggtgag aaaggtga                                                 18

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
gcaggtccag aacctccag                                                19

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
aaacacaaac ttgaacagct ac                                            22

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
atttgaggca gtttacatta tgg                                           23
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
atgcctcaca cggagactgt                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
agggctgtcc tgaataagca                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
tatttgaatc agtctgccga g                                            21

<210> SEQ ID NO 12
<211> LENGTH: 28
<212> TYPE: DNA
<213> ORGANISM: Artificial Sequence
<220> FEATURE:
<223> OTHER INFORMATION: Synthetic primer

<400> SEQUENCE: 12
atgtacctgt tataaggatg atattagt                                     28

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
accaggcact accgtaaaca ca                                           22

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ggtccgacct ggaaaatgct                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 15
cttcaccacc atggaggagg c                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ggcatggact gtggtcatga g                                              21

<210> SEQ ID NO 17
<211> LENGTH: 23
<212> TYPE: DNA
<213> ORGANISM: Artificial Sequence
<220> FEATURE:
<223> OTHER INFORMATION: Synthetic primer

<400> SEQUENCE: 17
acatcttcaa gtgctagaaa tgc                                            23

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
gaaatcttgg ctctcttggg                                                20

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
ccattcttca aggcttcaga g                                              21

<210> SEQ ID NO 20
<211> LENGTH: 19
<212> TYPE: DNA
<213> ORGANISM: Artificial Sequence
<220> FEATURE:
<223> OTHER INFORMATION: Synthetic primer

<400> SEQUENCE: 20
ggcgttaggg atctttggt                                                 19

<210> SEQ ID NO 21
<211> LENGTH: 18
<212> TYPE: DNA
<213> ORGANISM: Artificial Sequence
<220> FEATURE:
<223> OTHER INFORMATION: Synthetic primer

<400> SEQUENCE: 21
cctcacttcg cagctttg                                                  18
```

```
<210> SEQ ID NO 22
<211> LENGTH: 17
<212> TYPE: DNA
<213> ORGANISM: Artificial Sequence
<220> FEATURE:
<223> OTHER INFORMATION: Synthetic primer

<400> SEQUENCE: 22
gccgcaggaa acctgga                                                  17

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
gcttattgta gggaacgcag                                               20

<210> SEQ ID NO 24
<211> LENGTH: 18
<212> TYPE: DNA
<213> ORGANISM: Artificial Sequence
<220> FEATURE:
<223> OTHER INFORMATION: Synthetic primer

<400> SEQUENCE: 24
cgacagagca agactcag                                                 18

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
gcctgcgatg atttatactc ac                                            22

<210> SEQ ID NO 26
<211> LENGTH: 19
<212> TYPE: DNA
<213> ORGANISM: Artificial Sequence
<220> FEATURE:
<223> OTHER INFORMATION: Synthetic primer

<400> SEQUENCE: 26
aaacagagta agagagccg                                                19

<210> SEQ ID NO 27
<211> LENGTH: 17
<212> TYPE: DNA
<213> ORGANISM: Artificial Sequence
<220> FEATURE:
<223> OTHER INFORMATION: Synthetic primer

<400> SEQUENCE: 27
ctagggtgga agagccg                                                  17

<210> SEQ ID NO 28
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 28
gctgctatgg gcaaagtt                                                  18

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
cagttgtgtc tcccggtttt                                                20

<210> SEQ ID NO 30
<211> LENGTH: 30
<212> TYPE: DNA
<213> ORGANISM: Artificial Sequence
<220> FEATURE:
<223> OTHER INFORMATION: Synthetic primer

<400> SEQUENCE: 30
ggggaacctg gaggatggca agctgagaaa                                     30

<210> SEQ ID NO 31
<211> LENGTH: 25
<212> TYPE: DNA
<213> ORGANISM: Artificial Sequence
<220> FEATURE:
<223> OTHER INFORMATION: Synthetic primer

<400> SEQUENCE: 31
ggcctggtgg gggtgggagg aacat                                          25

<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32
gtggcacaga gtttagtga                                                 19

<210> SEQ ID NO 33
<211> LENGTH: 18
<212> TYPE: DNA
<213> ORGANISM: Artificial Sequence
<220> FEATURE:
<223> OTHER INFORMATION: Synthetic primer

<400> SEQUENCE: 33
tgggtactct tgcacttg                                                  18

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
tcttcaggtt ctgttgctcg                                                20
```

```
<210> SEQ ID NO 35
<211> LENGTH: 22
<212> TYPE: DNA
<213> ORGANISM: Artificial Sequence
<220> FEATURE:
<223> OTHER INFORMATION: Synthetic primer

<400> SEQUENCE: 35
gttaatcccg tctaccagtc tc                                            22

<210> SEQ ID NO 36
<211> LENGTH: 26
<212> TYPE: DNA
<213> ORGANISM: Artificial Sequence
<220> FEATURE:
<223> OTHER INFORMATION: Synthetic primer

<400> SEQUENCE: 36
ggataacatt gtactgggaa gggaca                                        26

<210> SEQ ID NO 37
<211> LENGTH: 30
<212> TYPE: DNA
<213> ORGANISM: Artificial Sequence
<220> FEATURE:
<223> OTHER INFORMATION: Synthetic primer

<400> SEQUENCE: 37
caaagtttct tttattcgta tgtgtgagca                                    30

<210> SEQ ID NO 38
<211> LENGTH: 17
<212> TYPE: DNA
<213> ORGANISM: Artificial Sequence
<220> FEATURE:
<223> OTHER INFORMATION: Synthetic primer

<400> SEQUENCE: 38
ggaaaggaga gtgcgtg                                                  17

<210> SEQ ID NO 39
<211> LENGTH: 26
<212> TYPE: DNA
<213> ORGANISM: Artificial Sequence
<220> FEATURE:
<223> OTHER INFORMATION: Synthetic primer

<400> SEQUENCE: 39
cactgcctgt aatatttgat gactaa                                        26

<210> SEQ ID NO 40
<211> LENGTH: 26
<212> TYPE: DNA
<213> ORGANISM: Artificial Sequence
<220> FEATURE:
<223> OTHER INFORMATION: Synthetic primer

<400> SEQUENCE: 40
atctgagcca agtagaagac cttttc                                        26

<210> SEQ ID NO 41
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 41
tctgcctgga ctaatctgca ag                                            22

<210> SEQ ID NO 42
<211> LENGTH: 17
<212> TYPE: DNA
<213> ORGANISM: Artificial Sequence
<220> FEATURE:
<223> OTHER INFORMATION: Synthetic primer

<400> SEQUENCE: 42
tccaagcgtg taagggt                                                  17

<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
gaagggactg agattggc                                                 18

<210> SEQ ID NO 44
<211> LENGTH: 22
<212> TYPE: DNA
<213> ORGANISM: Artificial Sequence
<220> FEATURE:
<223> OTHER INFORMATION: Synthetic primer

<400> SEQUENCE: 44
tttaacgtcg ttatggagac ga                                            22

<210> SEQ ID NO 45
<211> LENGTH: 25
<212> TYPE: DNA
<213> ORGANISM: Artificial Sequence
<220> FEATURE:
<223> OTHER INFORMATION: Synthetic primer

<400> SEQUENCE: 45
gctaatactc gttaataaat caccg                                         25

<210> SEQ ID NO 46
<211> LENGTH: 22
<212> TYPE: DNA
<213> ORGANISM: Artificial Sequence
<220> FEATURE:
<223> OTHER INFORMATION: Synthetic primer

<400> SEQUENCE: 46
tttaatgttg ttatggagat ga                                            22

<210> SEQ ID NO 47
<211> LENGTH: 29
<212> TYPE: DNA
<213> ORGANISM: Artificial Sequence
<220> FEATURE:
<223> OTHER INFORMATION: Synthetic primer

<400> SEQUENCE: 47
accactaata ctcattaata aatcaccac                                     29
```

```
<210> SEQ ID NO 48
<211> LENGTH: 29
<212> TYPE: DNA
<213> ORGANISM: Artificial Sequence
<220> FEATURE:
<223> OTHER INFORMATION: Synthetic primer

<400> SEQUENCE: 48
aaggaagttt tagtatagaa tttttaaat                                29

<210> SEQ ID NO 49
<211> LENGTH: 24
<212> TYPE: DNA
<213> ORGANISM: Artificial Sequence
<220> FEATURE:
<223> OTHER INFORMATION: Synthetic primer

<400> SEQUENCE: 49
aaaaaaataa ataaactccc ctcc                                     24

<210> SEQ ID NO 50
<211> LENGTH: 25
<212> TYPE: DNA
<213> ORGANISM: Artificial Sequence
<220> FEATURE:
<223> OTHER INFORMATION: Synthetic primer

<400> SEQUENCE: 50
atttgttttt tgggtagtta aaggt                                    25

<210> SEQ ID NO 51
<211> LENGTH: 27
<212> TYPE: DNA
<213> ORGANISM: Artificial Sequence
<220> FEATURE:
<223> OTHER INFORMATION: Synthetic primer

<400> SEQUENCE: 51
ccaactatct tcatcttaat aacatcc                                  27
```